(12) United States Patent
Siu et al.

(10) Patent No.: US 10,307,076 B2
(45) Date of Patent: Jun. 4, 2019

(54) SYSTEM AND METHOD FOR DETECTION OF COLLAGEN USING MAGNETIC RESONANCE IMAGING

(71) Applicant: SUNNYBROOK RESEARCH INSTITUTE, Toronto, ON (CA)

(72) Inventors: Adrienne Grace Siu, Toronto (CA); Graham A. Wright, Toronto (CA)

(73) Assignee: Sunnybrook Research Institute, Toronto, ON (CA)

( * ) Notice: Subject to any disclaimer, the term of this patent is extended or adjusted under 35 U.S.C. 154(b) by 172 days.

(21) Appl. No.: 15/547,307

(22) PCT Filed: Jan. 27, 2016

(86) PCT No.: PCT/CA2016/050065
§ 371 (c)(1),
(2) Date: Jul. 28, 2017

(87) PCT Pub. No.: WO2016/119054
PCT Pub. Date: Aug. 4, 2016

(65) Prior Publication Data
US 2018/0020946 A1 Jan. 25, 2018

Related U.S. Application Data

(60) Provisional application No. 62/110,000, filed on Jan. 30, 2015.

(51) Int. Cl.
*A61B 5/055* (2006.01)
*G01R 33/50* (2006.01)
(Continued)

(52) U.S. Cl.
CPC .......... *A61B 5/055* (2013.01); *A61B 5/14546* (2013.01); *A61B 5/7278* (2013.01); *G01R 33/4816* (2013.01); *G01R 33/50* (2013.01)

(58) Field of Classification Search
CPC ... A61B 5/055; A61B 5/7278; A61B 5/14546; G01R 33/50; G01R 33/4816
See application file for complete search history.

(56) References Cited

U.S. PATENT DOCUMENTS 7,468,605 B2 12/2008 Yu et al.
7,602,184 B2 10/2009 Du
(Continued)

FOREIGN PATENT DOCUMENTS

EP 2423701 2/2012
EP 2511696 10/2012

OTHER PUBLICATIONS

Tyler, D. J. et al., J. Mag. Reson. Imag. 25, 279-289 (2007).
(Continued)

*Primary Examiner* — G. M. A Hyder
(74) *Attorney, Agent, or Firm* — Hill & Schumacher

(57) ABSTRACT

Systems and methods are provided for detecting collagen within tissue using magnetic resonance imaging. In some embodiments, pulse sequences are employed to measure signals at multiple TE values including ultra-short echo times, and the TE dependence of the measured signal is fitted to a mathematical function including at least two decay terms, where the first (initial) decay term is modulated and is associated with the presence of collagen. In another example embodiment, spectroscopy or spectroscopic imaging is employed to measure the free induction decay within at least one region of interest, and the time-dependence of the measured signal is fitted to a mathematical function including at least two decay terms, where the first decay term is modulated and is associated with the presence of collagen. In some embodiments, the methods described herein may be employed for the detection and/or assessment of myocardial fibrosis.

35 Claims, 17 Drawing Sheets

(51) Int. Cl.
*A61B 5/145* (2006.01)
*G01R 33/48* (2006.01)
*A61B 5/00* (2006.01)

(56) References Cited

U.S. PATENT DOCUMENTS

| | | | |
|---|---|---|---|
| 8,034,898 | B2 | 10/2011 | Caravan et al. |
| 2005/0240096 | A1* | 10/2005 | Ackerman ............. A61B 5/055 600/410 |
| 2007/0293656 | A1* | 12/2007 | Caravan ................ A61B 5/055 530/317 |
| 2008/0039710 | A1* | 2/2008 | Majumdar ............. A61B 5/055 600/410 |
| 2008/0058636 | A1 | 3/2008 | Caravan et al. |
| 2010/0129292 | A1 | 5/2010 | Jerosch-Herold et al. |
| 2014/0121492 | A1 | 5/2014 | Boernert et al. |
| 2014/0303479 | A1 | 10/2014 | Neeman et al. |

OTHER PUBLICATIONS

Gatehouse, P. D. et al., Clinical Radiology 58: 1-19 (2003).
Robson, M. D. et al., J Comput Assist Tomogr 27, 825-846 (2003).
De Jong, S. et al., Proc. Intl. Soc. Mag. Reson. Med. 19 (2011).
X. Dai and J. Ronsky, "The Study of Knee Tibiofemoral Condyle Cartilage Relaxation Characters Based on Quantitative MR T2 Imaging," IEEE, 2013.
R. S. Macleod, J. Blauer, E Kholmovski, R. Ranjan, N. Marrouche, N. Trayanova, K. McDowell, and G. Plank, "Subject specific, image based analysis and modeling in patients with atrial fibrillation from MRI," IEEE, 2012.
L. V. Krasnosselskaia, "Mechanisms for Short T 2 and T * 2 in Collagen-Containing Tissue," vol. 1, pp. 625-632, 2012.
Y. Han, T. Liimatainen, R. C. Gorman, and W. R. T. Witschey, "Assessing Myocardial Disease Using T1p MRI," Curr. Cardiovasc. Imaging Rep., vol. 7, No. 2, pp. 1-9, 2014.
S. P. Zhong, M.N. Helmus, S. R. Smith, B. E. Hammer, "Magnetic Resonance Imaging of a Medical Device and Proximate Body Tissue," WO 2005/101045 A1. 2005.
M. K. Manhard, R. A. Horch, K. D. Hharkins, D. F. Gochberg, J. S. Nyman, and M. D. Does, "Validation of quantitative bound- and pore-water imaging in cortical bone," Magn. Reson. Med., vol. 71, No. 6, pp. 2166-2171, 2014.
De Jong S1, Zwanenburg JJ, Visser F, Der Nagel Rv, Van Rijen HV, Vos Ma, De Bakker Jm, Luijten PR., J Mol Cell Cardiol. Dec. 2011;51(6):974-9. doi: 10.1016/j.yjmcc.2011.08.024. Epub Sep. 1, 2011 Direct detection of myocardial fibrosis by MRI.
B. J. Van Nierop, J. L. Nelissen, N. A. Bax, A. G. Motaal, L. De Graaf, K. Nicolay, and G. J. Strijkerss, "In vivo ultra short TE (UTE) MRI detects diffuse fibrosis in hypertrophic mouse hearts," Proc Int Soc Magn Reson Med, Abstract #1360. Apr. 2013.
Sanne De Jongde Jong et al., Direct detection of myocardial fibrosis by MRI, Journal of Molecular Cellular Cardiology, vol. 51, Issue 6, Dec. 2011, pp. 974-979, ISSN 0022-2828, http://dx.doi.org/10.1016/j.yjmcc.2011.08.024.
Wehrli, Felix, Magnetic resonance of calcified tissues, Journal of Magnetic Resonance, 229, Apr. 2013, pp. 35-48, ISSN 1090-7807, http://dx.doi.org/10.1016/j.jmr.2012.12.011.
Siu et al., Characterization of the ultra-short echo time magnetic resonance (UTE MR) collagen signal associated with myocardial fibrosis. Journal of Cardiovascular Magnetic Resonance. 2015;17(Suppl 1):Q7. doi:10.1186/1532-429X-17-S1-Q7.
Van Nierop et al. (2015) Assessment of Myocardial Fibrosis in Mice Using a T2*-Weighted 3D Radial Magnetic Resonance Imaging Sequence. PLoS ONE 10(6): e0129899. doi: 10.1371/journal.pone.0129899.
International Search Report (PCT/CA2016/050065) dated May 12, 2016.
Written Opinion (PCT/CA2016/050065) dated May 12, 2016.

* cited by examiner

| UTE parameters | Collagen solutions | Heart tissue |
|---|---|---|
| Repetition time | 30 ms | 30 ms |
| Flip angle | 15° | 15° |
| Number of averages | 1 | 1 |
| Number of projections | 12,753 | 12,753 |
| Polar undersampling factor | 1 | 1 |
| Field-of-view | 50 mm x 50 mm x 50 mm | 10 mm x 10 mm x 10 mm |
| Matrix size | 64 x 64 x 64 | 64 x 64 x 64 |
| Spatial resolution | 0.781 mm isotropic | 0.156 mm isotropic |
| TEs | 0.02, 0.06, 0.1, 0.14, 0.18, 0.22, 0.25, 0.3, 0.35, 0.4, ..., 4.85, 4.9, 4.95, 5, 10, 15, 20, 25 ms<br><br>(TEs from 0.25 to 5 ms separated by intervals of 0.05 ms) | 0.02, 0.025, 0.030, 0.035, ..., 1.985, 1.99, 1.995, 2, 3, 5, 10, 15, 20, and 25 ms<br><br>(TEs from 0.02 ms to 2 ms separated by intervals of 0.005 ms) |
| Number of TEs | 106 | 403 |
| Scan time per TE | ~ 6.5 mins | ~ 6.5 mins |
| Total scan time | ~ 11.5 hours | ~ 43.7 hours |

FIG. 4

| NSPECT parameters | 50 % collagen solution |
|---|---|
| Repetition time | 1,000 ms |
| Number of averages | 10 |
| Number of repetitions | 1 |
| Acquisition time | 262.14 ms |
| Number of points | 32,768 |
| Dwell time | 0.008 ms |
| Spectral resolution | 3.8147 Hz |
| Spectral width | 125,000 Hz |
| Scan time | 10 s |

FIG. 5

| Parameter | Initial estimate | Lower bound | Upper bound |
|---|---|---|---|
| $S_{0,long}$ | 40,000 AU | 0 | 1,000,000 AU |
| $T_2^*{}_{long}$ | 20 ms | 0 | 50 ms |
| $S_{0,collagen}$ | 40,000 AU | 0 | 1,000,000 AU |
| $T_2^*{}_{collagen}$ | 1 ms | 0 | 4 ms |
| $f_{collagen}$ | 1 kHz | 0 | 10 kHz |

FIG. 6

| Collagen solution conc. (% g/mL) | 0 | 2.5 | 5 | 10 | 20 | 30 | 40 | 50 | Mean ± standard deviation (10 % to 50 % conc.) |
|---|---|---|---|---|---|---|---|---|---|
| $T_2^*_{long}$ (ms) | 38.2* | 33.8 ± 0.3 | 33.2 ± 0.4 | 30.5 ± 0.3 | 21.1 ± 0.3 | 17.8 ± 0.3 | 14.0 ± 0.2 | 11.3 ± 0.2 | --- |
| $T_2^*_{collagen}$ (ms) | 4* | 5 x 10$^{-3}$* | 3 ± 2 | 0.8 ± 0.1 | 0.75 ± 0.08 | 0.71 ± 0.07 | 0.76 ± 0.07 | 0.71 ± 0.07 | 0.75 ± 0.05 |
| $f_{collagen}$ (kHz) | 4 x 10$^{-12}$* | 2* | 1.10 ± 0.03 | 1.07 ± 0.02 | 1.06 ± 0.02 | 1.06 ± 0.02 | 1.06 ± 0.01 | 1.06 ± 0.02 | 1.061 ± 0.004 |
| Collagen signal fraction from UTE MRI (%) | 1 x 10$^{-7}$* | 0.1* | 0.6 ± 0.3 | 4.2 ± 0.4 | 8.6 ± 0.6 | 13.0 ± 0.9 | 16 ± 1 | 20 ± 1 | --- |

FIG. 9

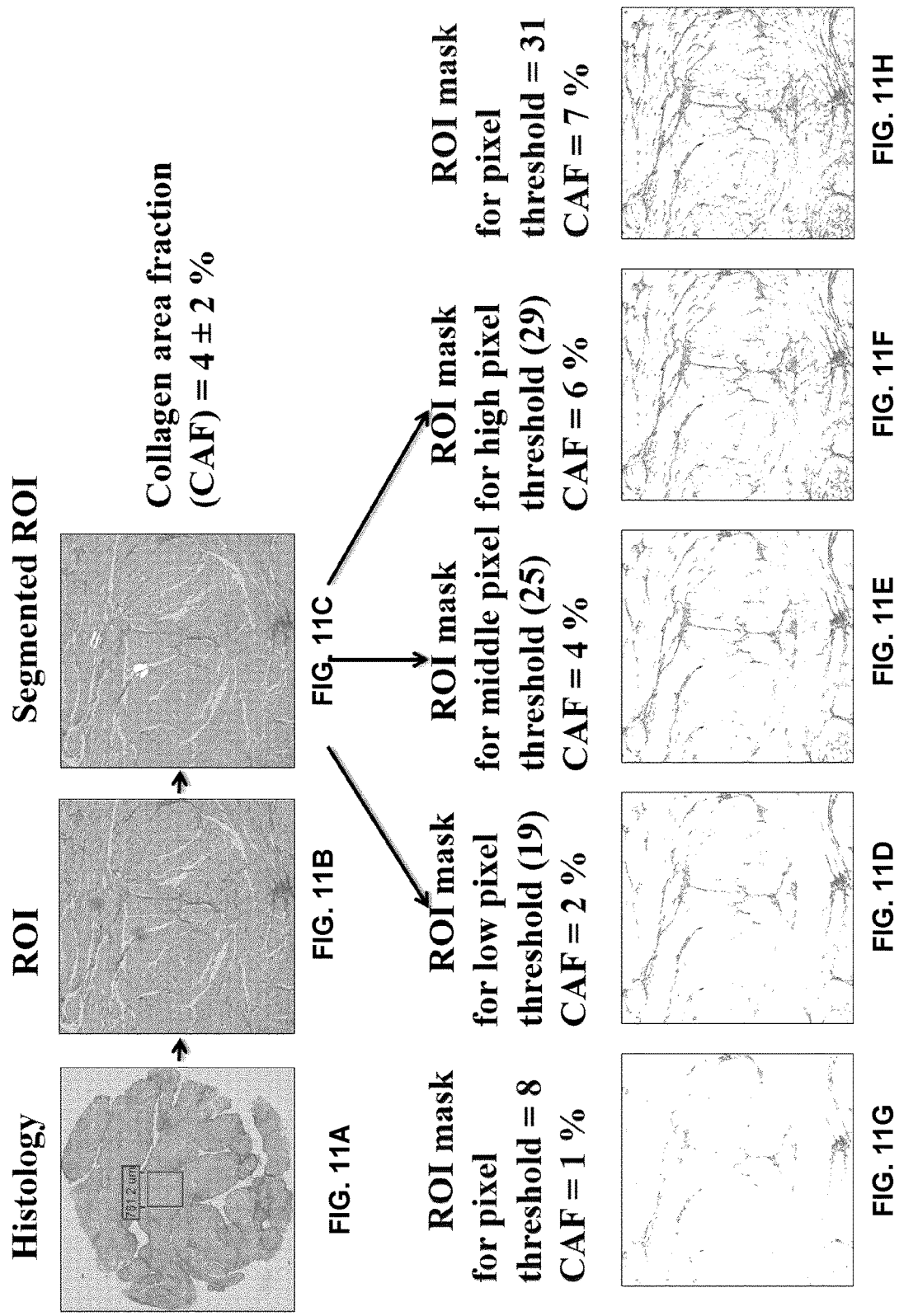

|  | Mean ± standard deviation | Range |
|---|---|---|
| $T_2^*{}_{collagen}$ (ms) | 1.03 ± 0.07 | 0.95 to 1.12 |
| $f_{collagen}$ (kHz) | 1.12 ± 0.05 | 1.09 to 1.19 |
| Collagen signal fraction (%) | 1.0 ± 0.2 | 0.7 to 1.3 |

FIG. 13 ically using a three-component $T_2^*$ model at 9.4 T [14]. Van
SYSTEM AND METHOD FOR DETECTION OF COLLAGEN USING MAGNETIC RESONANCE IMAGING

CROSS-REFERENCE TO RELATED APPLICATION

This application is a National Phase application claiming the benefit of the international PCT Patent Application No. PCT/CA2016/050065, filed on Jan. 27, 2016, in English, which claims priority to U.S. Provisional Application No. 62/110,000, titled "SYSTEM AND METHOD FOR DETECTION OF COLLAGEN USING MAGNETIC RESONANCE IMAGING" and filed on Jan. 30, 2015, the entire contents of which are incorporated herein by reference.

BACKGROUND

The present disclosure relates to magnetic resonance imaging. More particularly, the present disclosure relates to methods of collagen detection using magnetic resonance imaging systems.

Myocardial fibrosis is defined by increased collagen synthesis in the heart by fibroblasts and myofibroblasts, either in a local or diffuse distribution [1]. Of particular interest is diffuse myocardial fibrosis, which presents an imaging challenge due to the uniform interspersion of collagen throughout the myocardium. While diffuse myocardial fibrosis is a normal process of aging, it is accelerated in diseases, including aortic stenosis, cardiomyopathy, and hypertension [2]. Collagen volume fractions of 10-40% may result from diffuse myocardial fibrosis [3], compared to the 2-6% collagen volume fraction of a normal heart [3], [4]. The consequence is impaired ventricular systolic function and stiffness, ultimately leading to heart failure [1], [5]. Heart failure is a widely prevalent disease, estimated to affect 500,000 Canadians, and carrying a five-year survival rate of 50% [6].

In order to prevent late-stage heart failure, there is a need for a non-invasive and accurate measure of diffuse myocardial fibrosis. The gold standard for the diagnosis of diffuse myocardial fibrosis is endomyocardial biopsy, which measures the collagen volume fraction to evaluate the disease extent; however, this method is invasive and susceptible to sampling error [7]. Cardiovascular magnetic resonance (CMR) techniques have shown promise for the characterization of myocardial fibrosis, and include late gadolinium enhancement (LGE) and $T_1$ mapping. Nevertheless, LGE is unsuitable for the detection of diffuse myocardial fibrosis, as the uniform distribution of collagen renders it difficult to achieve a clear signal intensity difference between healthy and fibrotic tissue [8]. $T_1$ mapping with gadolinium-based contrast agents, by contrast, can be used to measure the extracellular volume fraction in diffuse myocardial fibrosis [9], [10]; however, this method is governed by gadolinium kinetics and is not specific to collagen [1], [7]. An imaging technique that can directly detect and quantify collagen would, hence, be of benefit to the diagnosis of diffuse myocardial fibrosis.

Ultra-short echo time (UTE) is an intrinsic MR contrast technique that can detect tissues with short $T_2^*$ relaxation times, which are normally indiscernible using conventional pulse sequences. As collagen has a short $T_2^*$, this technique has been employed to image many collagen-containing tissues, including tendon, cartilage, ligaments, menisci, and bone. Ultra-short TEs are typically less than a few ms (e.g. 2 ms) where the lowest TE achievable is limited by the delay in switching between the radiofrequency excitation and the data acquisition. Recent literature by De Jong et al. [12] and Van Nierop et al. [13], [14] has demonstrated the feasibility of detection of myocardial fibrosis using UTE MRI. Using an MR image subtraction method, De Jong et al. and Van Nierop et al. showed that UTE MRI can be used for the qualitative delineation of myocardial infarct at 7 T and 9.4 T, respectively [12], [13].

The study of De Jong et al. predicted that the collagen short $T_2^*$ component originated from the hydration layer water surrounding collagen [12]. In a different study, Van Nierop et al. modelled diffuse myocardial fibrosis quantitatively using a three-component $T_2^*$ model at 9.4 T [14]. Van Nierop et al. found a signal with a short $T_2^*$ of ~0.8 ms and a chemical shift of ~3 ppm, which they attributed to lipids.

SUMMARY

Systems and methods are provided for detecting collagen within tissue using magnetic resonance imaging. Example methods of acquisition include sampling a discrete time signal (e.g. ultra-short TE), and sampling a continuous time signal (e.g. spectroscopy and spectroscopic imaging). In some embodiments, ultra-short TE pulse sequences are employed to measure signals at multiple TE values, and the TE dependence of the measured signal is fitted to a mathematical function including at least two decay terms, where the first decay term is modulated and is associated with the presence of collagen. In another example embodiment, spectroscopy or spectroscopic imaging is employed to measure the free induction decay within at least one region of interest, and the time-dependence of the measured signal is fitted to a mathematical function including at least two decay terms, where the first decay term is modulated and is associated with the presence of collagen. In some embodiments, the methods described herein may be employed for the detection and/or assessment of myocardial fibrosis.

Accordingly, in a first aspect, there is provided a method of detecting the presence of collagen in tissue using magnetic resonance imaging, the method comprising:

obtaining a series of images at a plurality of TE values, wherein at least a subset of said images are acquired with ultra-short TE values that are suitable for sampling an initial decay having a time-dependent modulation associated with collagen;

processing the series of images and fitting the dependence of the signal on TE to a function comprising:
  a first decay term associated with the presence of collagen, wherein the first decay term is modulated at a modulation frequency associated with the presence of collagen; and
  a second decay term, the second decay term having a longer decay than the first term; and processing the fitting parameters to provide a measure associated with an amount of collagen.

In another aspect, there is provided a method of detecting the presence of collagen in tissue using magnetic resonance imaging, the method comprising:

performing spectroscopy or spectroscopic imaging and measuring the free induction decay within at least one region of interest;

fitting the dependence of the signal on time to a function comprising:
  a first decay term associated with the presence of collagen, wherein the first decay term is modulated at a modulation frequency; and a second decay term, the second decay term having a longer decay than the first term; and processing the fitting parameters to provide a measure associated with an amount of collagen.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIG. 4 is a table listing the UTE imaging parameters for the collagen solutions and heart tissue.

FIG. 5 is a table listing the NSPECT (non-localized spectroscopy) parameters for the 50% collagen solution.

FIG. 6 is a table providing initial values of the fit parameters in eqn. 1.

FIG. 7A is an axial UTE image at TE=0.02 ms. The 10-×8-pixel ROI is the outlined rectangle. FIG. 7B is an axial UTE image at TE=25 ms, with the indicated 10-×8-pixel ROI.

FIG. 9 is a table listing the collagen solution fit parameters. The uncertainties are the standard errors. Values marked by asterisks (*) could not be calculated accurately, owing to non-unique fit solutions and fit instability.

FIG. 10A plots the real NSPECT spectrum of the 50% collagen solution. FIG. 10B provides a detailed view of the spectrum from FIG. 10A, magnified 10 times. FIG. 10C plots the real spectrum of the 50% collagen solution, reconstructed from the fit parameters derived from analysis of UTE images. FIG. 10D provides a detailed view of the spectrum from FIG. 10C, magnified 10 times.

FIGS. 11A-H illustrate the workflow of histological analysis. FIG. 11A is a histological image of the heart sample, stained with Picrosirius Red. The 781.2 μm×781.2 μm ROI is outlined. FIG. 11B is an enlarged view of the ROI. FIG. 11C shows the ROI with nuclei and particle contamination removed. FIG. 11D-11F show ROI masks for quantification of the collagen area fraction. The collagen area fractions were produced from the pixel thresholds indicated in parentheses. Based on the three pixel thresholds specified, a collagen area fraction of 4±2% was determined for the ROI. FIGS. 11G and 11H are ROI masks that generated collagen area fractions of 1% and 7%, respectively, beyond the uncertainty range of the 4±2% collagen area fraction determined for the ROI. As observed, a collagen area fraction of 1% does not reasonably include all of the collagen pixels, when compared with the segmented ROI in (c). By contrast, a collagen area fraction of 7% includes background pixels that are not collagen.

FIGS. 12A and 12B are axial UTE images at TE=0.02 ms and TE=25 ms, respectively. The rectangle outlines the 781.2 μm×781.2 μm (5-×5-pixel) ROI. FIG. 12C plots the $T_2^*$ decay for TEs 0.02 ms to 2 ms, with a detailed view along the y-axis. FIG. 12D plots the $T_2^*$ decay for TEs 0.02 ms to 25 ms. In the fit, the upper bound of $T_2^*_{collagen}$ was restricted to 1.1165 ms.

FIG. 13 is a table describing collagen parameters from $T_2^*$ analyses of the five heart tissue ROIs. It is noted that $T_2^*$ fitting was performed for each ROI individually, before the mean±standard deviation of each parameter was taken over all five ROIs. The range indicates the span of values across the five ROIs.

DETAILED DESCRIPTION

Figure 1:
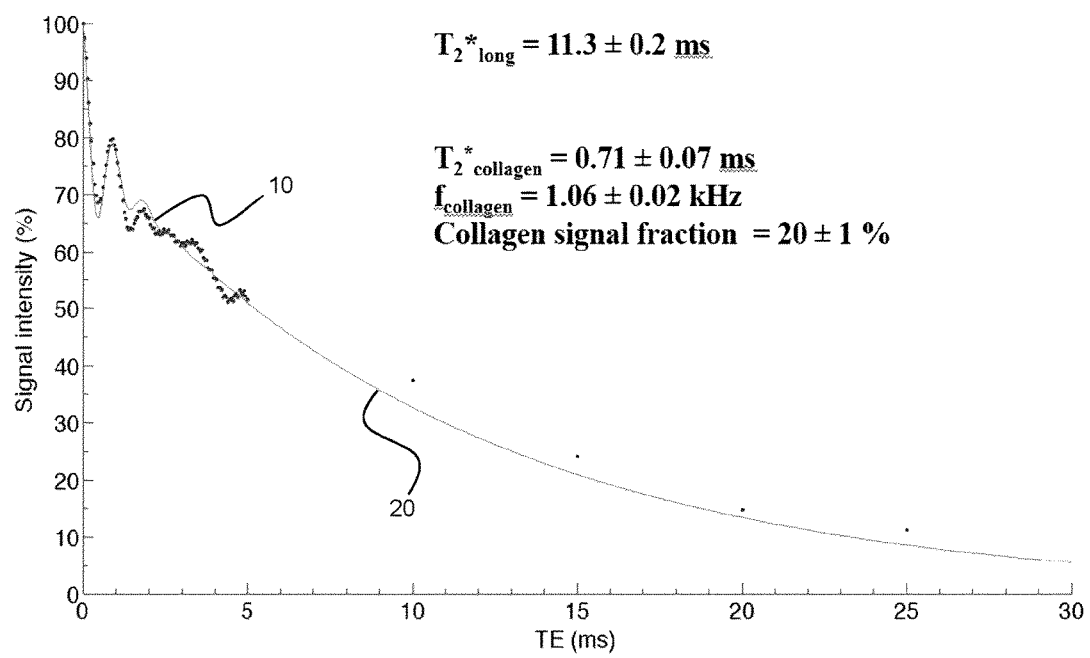
FIG. 1 is a plot of measured $T_2^*$ decay for a 50% collagen solution along with a fitted curve according to a bi-exponential model.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrases "ultra-short TE" and "UTE", when employed to describe a TE, refer to TE values that are less than approximately 2 ms. The acquisition of UTE images can be performed using a radial k-space acquisition protocol, as described in detail below. In some embodiments of the present disclosure, measurements are made for both ultra-short TE values, and for longer TE values (i.e. TE values greater than approximately 2 ms), in order to measure fast decaying components and to differentiate them from slowly decaying components, such that a residual signal at later echo times can be observed (at which time there should be negligible contributions from the fast-decaying components). Using information from both UTE acquisitions and those at longer TEs, one can separate the faster decaying components from the slower decaying components. It will be understood that the longer TE acquisitions may be obtained using a radial k-space acquisition method, or using other acquisition methods that are feasible for such longer TE values.

As noted above, in a previous study, the $T_2^*$ characterization of diffuse myocardial fibrosis in a rat model was performed by Van Nierop et al. [14] at 9.4 T. In the Van Nierop study, a modulated decay was observed, with a decay constant of 0.8±0.5 ms and a shift of −3.25 ppm (no uncertainty reported), respectively. This component was attributed to lipids by Van Nierop et al.

The present inventors questioned the methods and interpretation of the Van Nierop study, noticing that the lipid $T_2^*$ of Van Nierop et al. was shorter than previously reported lipid $T_2^*$ values. For example, it has been demonstrated that the $T_2^*$ of lipids can be approximately 50 ms [15]. In order to explain, and re-interpret the findings of Van Nierop et al., the present inventors hypothesized that the origin of the short modulated $T_2^*$ signal in the Van Nierop study was the protons in the collagen molecule.

It is noted that the $T_2^*$ components associated with collagen have several potential origins including: (1) the protons in the collagen molecule, (2) the protons belonging to the hydration water layer attached to the collagen strands, and (3) the protons from the free water surrounding collagen [16]. In order to confirm the hypothesis that the fast modulated component of the Van Nierop study was collagen protons, the present inventors performed ultra-short TE imaging studies of collagen solutions having known concentration. Such solutions are absent of lipids, and the presence of the oscillatory rapid decay in TE signal plot would be consistent with the hypothesis that the source of such behaviour is not lipids, and is instead the collagen protons. The objective of the collagen solution study was therefore to isolate and characterize signal from collagen via UTE MRI.

A representative TE-dependent graph, for a collagen concentration of 50%, obtained at 7 T, is shown in FIG. 1 (the details of the experimental and analytical methods are provided in the Examples section below). The graph clearly shows the presence of the fast modulated decay term 10, followed by a slower exponential decay 20, which validates the hypothesis that the short $T_2^*$ component previously measured in myocardial fibrosis [12], [14] originates from the protons belonging to the collagen molecule.

These collagen protons have a unique chemical shift relative to surrounding water hydration layers. In order to quantify the amount of collagen present in imaged tissue, a bi-exponential $T_2^*$ model of myocardial fibrosis was developed, which accounts for the chemical shift of collagen protons. Accordingly, in some embodiments, a simplified bi-exponential $T_2^*$ model is sufficient for the clinical detection of collagen within myocardial fibrosis. Rather than requiring accurate modelling of all $T_2^*$ exchange mechanisms that occur between collagen and cardiac muscle, some embodiments of the present disclosure employ a simplified bi-exponential $T_2^*$ model that is sufficient for the detection of collagen.

Kaflak-Hachulska et al. showed that the $^1$H MR spectrum of type I collagen powder from bovine Achilles tendon is characterized by a predominant peak at −3.2 ppm relative to water, analogous to a frequency of ~1 kHz at a magnetic field strength of 7 T [17]. As this chemical shift pertains to the protons in collagen, rather than bound water, one may use this property to model the MR signal from collagen itself. The modulation frequency observed in FIG. 1 is consistent with this chemical shift at 7 T.

In one example embodiment, the ultra-short TE signal decay of collagen is characterized by bi-exponential $T_2^*$ decay with an oscillation term:

$$S(TE)=S_{0,collagen}\cos(2\pi f_{collagen}TE)e^{-TE/T_2^*_{collagen}}+S_{0,long}e^{-TE/T_2^*_{long}} \quad [1]$$

where $S_{0,collagen}$, $f_{collagen}$, and $T_2^*_{collagen}$ refer to the initial signal intensity, resonance frequency (relating to the chemical shift of the predominant peak for collagen relative to water), and $T_2^*$ of protons in the collagen molecule; and $S_{0,long}$ and $T_2^*_{long}$ denote the initial signal intensity and $T_2^*$ of the long $T_2^*$ component, attributed to water in cardiomyocytes.

While the MR signal is inherently complex, magnitude images are typically analyzed in the clinic, resulting in real and nonnegative magnitude signal data. It is for this reason that the proposed $T_2^*$ signal equation is real, rather than complex; the approximation holds true, assuming that the collagen signal is small compared to the long $T_2^*$ (cardiac muscle) signal.

The present example embodiment, involving a first modulated decay term, and a second decay term, does not include intermediate $T_2^*$ components due to exchange, under the assumption that exchange processes are slow relative to the $T_2^*$s of collagen and collagen-associated water. The magnetization exchange rates of cartilage (which is mainly composed of collagen) with a liquid pool, and cardiac muscle with a liquid pool, are 59 s$^{-1}$ and 52 s$^{-1}$, respectively [18]. Thus, the total exchange rate between collagen and cardiac muscle should be 111 s$^{-1}$, based on existing literature. In the present two-pool $T_2^*$ model, collagen has an expected $T_2^*$ of ~1 ms and an offset frequency of ~1 kHz; muscle, by contrast, has an expected (long) $T_2^*$ of ~35 ms and an offset frequency of 0 kHz.

According to the definition of slow exchange between two pools with different resonance frequencies, the following must hold for the total exchange rate (k) [19]:

$$k \ll \left| \frac{1}{T_2^*_{collagen}} - \frac{1}{T_2^*_{long}} \right| \approx 971 s^{-1} \quad [2a]$$

$$k \ll |f_{collagen} - f_{long}| \approx 1000 S^{-1} (Hz) \quad [2b]$$

where the expressions have been evaluated, based on the expected values for the $T_2^*$s and frequencies of the two pools. In this case, the exchange rate of 111 s$^{-1}$ based on existing literature satisfies both Equations [2a] and [2b]. Hence, without intending to be limited by theory, it is hypothesized that the proposed two-pool $T_2^*$ model in the absence of exchange is a suitable and sufficient model for capturing the dominant behaviour. Given the frequency shift and short $T_2^*$ of protons in collagen, it is believed that the collagen $T_2^*$ component will be distinctive from the long $T_2^*$ component. Therefore, the present example bi-exponential model involving relatively few parameters may be useful in characterizing the collagen signal in a clinically practical method with limited data. This would aid in the identification of myocardial fibrosis and the determination of severity.

As described in the Examples section below, the bi-exponential model was first validated in collagen solutions, where the chemical shift and $T_2^*$ of collagen were evaluated, and the collagen signal fractions determined by UTE MRI are correlated with the known concentrations in order to establish a calibration relation between the ultra-short TE signal fraction and the collagen concentration. As described below, this relationship allows for the determination of the quantity of collagen in a tissue sample. The Examples also demonstrate how the bi-exponential model has been successfully applied to a sample of ex vivo canine heart tissue, where the chemical shift and $T_2^*$ properties observed in the collagen solutions are verified.

Figure 2A:
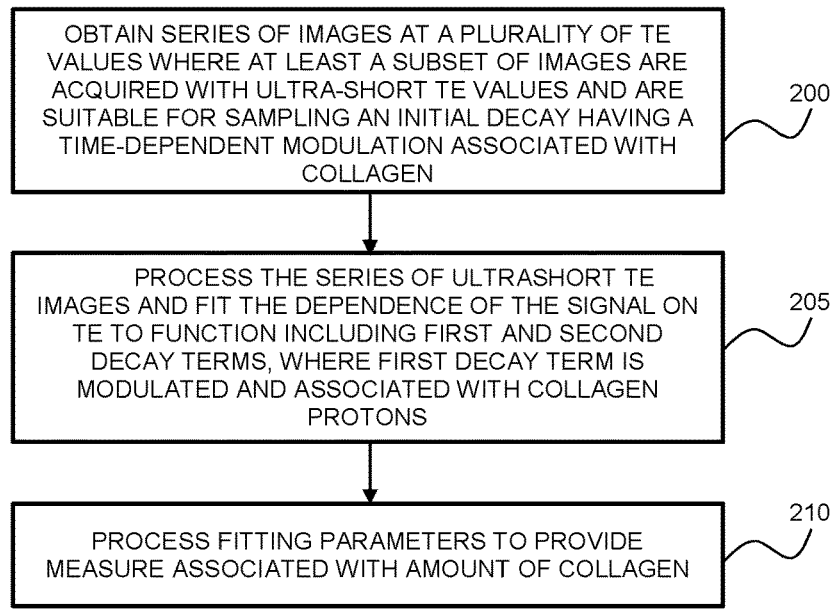
FIG. 2A is a flow chart illustrating an example method for detecting the presence of collagen in tissue using ultra-short TE magnetic resonance imaging.

FIG. 2A is a flow chart illustrating an example method for determining a measure associated with an amount of collagen in a tissue sample using ultra-short TE magnetic resonance imaging. In step 200, a series of images are obtained, wherein a subset possesses ultra-short TE values; the ultra-short TE values are suitable for sampling an initial (fast) decay having a time-dependent modulation associated with collagen. In other words, TE signals are obtained with temporal density that is sufficiently high to sample a modulation in the time dependence of the signal associated with the initial (fast) decaying component. For example, referring to FIG. 1A, the temporal density of data points in the vicinity of 0-2 ms, where the oscillatory (modulated) component is appreciable in signal intensity, should be sufficiently high to sample the ~1 kHz modulation signal that is observed.

In step 205, the series of ultra-short TE images are processed to fit the TE dependence of the signals according to a function that includes at least a first decay term and a second decay term, where the first decay term is modulated at a modulation frequency, and where the first term is associated with collagen protons. In other words, the time dependence of the measured signals is fitted to a function that includes, at least, the terms shown in eqn. 1.

The fitting parameters that are obtained from the fitting process are then employed to provide a measure associated with the amount of collagen, as shown at step 210. It will be understood that the fitting may be performed on a per pixel basis (i.e. fitting the time dependence of the signal of a given pixel), or may be performed by averaging the signals of several pixels over a selected region prior to fitting the time dependence of the signal to the function.

In one example implementation, the amplitude fitting parameters $S_{0,collagen}$ and $S_{0,long}$ may be employed to determine the collagen signal fraction as:

$$\text{Collagen signal fraction} = \frac{S_{0,collagen}}{S_{0,collagen} + S_{0,long}} \times 100\% \quad [1a]$$

and the collagen signal fraction may be employed to determine the concentration of collagen in the imaged tissue, using a calibration curve, look up table, or other calibration data. An example of such a calibration is provided in the Examples section below. For example, calibration data can be obtained by measuring the collagen signal fraction for a set of standard solutions having known concentrations of collagen.

In one example embodiment, the collagen signal amplitude and/or signal fraction may be compared to one or more threshold values in order to provide a discrete measure of the amount of collagen present in the imaged tissue. For example, diseased states of diffuse myocardial fibrosis are characterized by collagen volume fractions of over 10%. To this regard, it is of particular clinical interest to identify cases where the collagen occupies more than 10% of the tissue volume. For example, signals may be compared to multiple thresholds in order to distinguish between less diseased states (e.g. 10% collagen volume fractions) vs. more diseased states (e.g. 40% collagen volume fractions). Collagen volume fractions less than 10% may be deemed as healthy and are generally not critical for diagnosis.

It is noted that eqn. 1 has 5 fitted parameters, such that at least 5 points are required by the fitting algorithm to resolve the values of the fitted parameters. Accordingly, at least 3 points are needed to determine the collagen T2*, resonance frequency, and associated signal fraction; and at least 2 points to characterize the long T2* and associated signal fraction. However, in one example implementation, the relative signal fraction of collagen can be obtained without requiring a separate amplitude factor by modifying eqn. 1 to become a 4-parameter function:

$$S(TE) = S_{0,collagen} \cos(2\pi f_{collagen} TE) e^{-TE/T_2^*_{collagen}} + (1 - S_{0,collagen}) e^{-TE/T_2^*_{long}} \quad [1b]$$

where the total signal has been normalized to 1. As there are only 4 fitted parameters, at least 4 points are needed to resolve the values of the fitted parameters. If one can fix the values of $f_{collagen}$ and $T_2^*_{collagen}$ based on previous experience, one could theoretically determine the remaining variables ($S_{0,collagen}$ and $T_2^*_{long}$) with as few as 2 points, but it is expected that using 3 or more points will be more robust. Alternatively, if one can fix the value of $f_{collagen}$ or $T_2^*_{collagen}$ based on previous experience, the remaining values would be $S_{o,collagen}$, $T_2^*_{long}$, and $T_2^*_{collagen}$ for fixing $f_{collagen}$; and $S_{o,collagen}$, $T_2^*_{long}$, and $f_{collagen}$ for fixing $T_2^*_{collagen}$. In both cases, one could determine the remaining values with as few as 3 points, but it is expected that using 4 or more points will be more robust.

The density of TE points may be configured to decrease with time, such that a higher density of TE points is provided near TE=0, in order to provide a sufficient point density to sample the modulated $T_2^*_{collagen}$ decay, while also providing a sparser temporal sampling of the second decay term, in order to provide an overall efficient sampling, and a low or minimal overall scanning time. In some embodiments, a lower density of TE points, with a time interval satisfying the Nyquist criteria for sampling the modulation, is provided for TE values less than approximately 5 ms, 4 ms, 3 ms, or 2 ms. In some embodiments, the TE point density is selected such that a sufficient number of points are provided for sampling the first modulated decay and the second decay, while maintaining an overall number of TE samples less than or equal to 15, 12, 10, 9, 8, 7, 6, 5 or 4 points.

In one example implementation, all fitting parameters are freely fitted. In other embodiments, one or more fitting parameters may be fixed to a pre-determined value, or constrained to lie within a pre-determined range of values. For example, $T_2^*_{collagen}$ value may be fixed at a value that has been previously measured by in-vivo measurements or ex-vivo measurements. In one example embodiment, $T_2^*_{collagen}$ may be fixed to a value between approximately 0.5 ms and 3.0 ms. In one example embodiment, $T_2^*_{collagen}$ may be constrained to a value between approximately 0.5 ms and 3.0 ms. In another example, the modulation frequency may be fixed to a value based on a chemical shift of approximately −3.4 ppm. In another example, the modulation frequency may be constrained to a range based on a chemical shift between approximately −2.6 and −4.0 ppm.

Figure 2B:
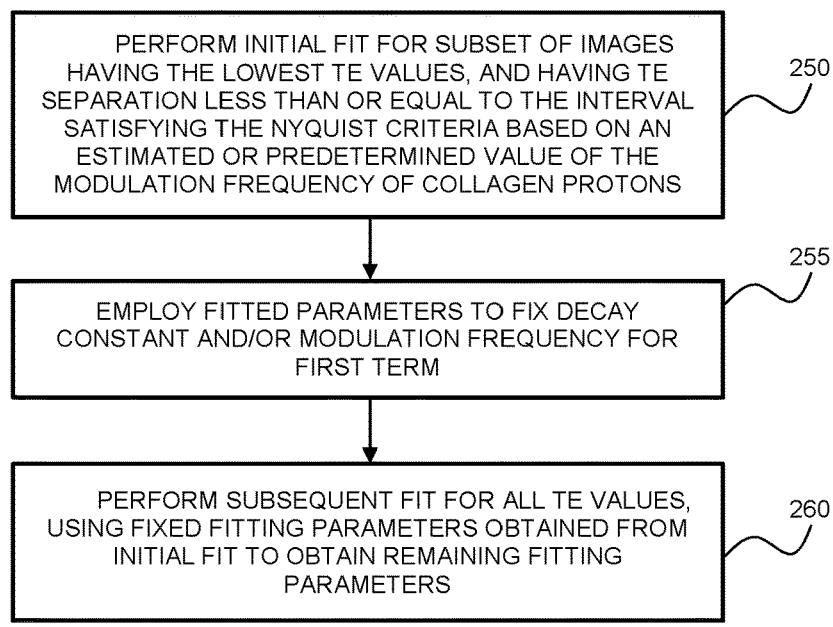
FIG. 2B is a flow chart illustrating another example method for detecting the presence of collagen in tissue using ultra-short TE magnetic resonance imaging, using a two-step fitting method.

FIG. 2B illustrates an example method of performing the fitting of the TE dependence of the ultra-short TE signal to the function, where the fitting is performed in two steps. It is noted that this two-step embodiment is merely provided as an example method of fitting, and that other methods may be employed without departing from the intended scope of the present disclosure. For example, the fitting method could be performed in one step if the data is of sufficient quality and/or quantity. However, this may place higher demands on data quality—i.e. the signal-to-noise ratio (SNR); an advantage of the two-step process is that it renders fitting the short component less sensitive to the specific nature of the long component.

In step 250, an initial fit is performed for a subset of the TE points having the lowest TE values (i.e. a subset of the images), where the subset of TE points has a temporal spacing that is suitable for sampling the modulation frequency in the fast decaying signal component due to collagen protons. This initial fit is employed to determine $T_2^*_{collagen}$ and to fix the value of $T_2^*_{collagen}$ for the subsequent fitting step, as shown at step 255. The value of the collagen proton modulation frequency may also be fixed based on the value obtained during this initial fitting step. In step 260, the remaining fitting parameters are fitted over the full TE range. In one example implementation of this method, the initial fitting may be performed based on image data within a region of interest that is known to contain collagen, expected to contain collagen, known to exhibit fibrosis, or expected to exhibit fibrosis. For example, when performing cardiac imaging to detect or assess fibrosis, the region of interest could include the left ventricle, while excluding regions with interfering signals such as the blood pool.

Although many of the examples provided herein relate to the use of a bi-exponential fitting function with only two terms, it will be understood that the two-term function is merely an example function, and that according to other non-limiting example embodiments, the function may be modified by the addition of one or more additional terms. There are multiple embodiments of the fitting function used to characterize the decay term and modulation frequency associated with collagen. These embodiments include, but are not limited to, the domain in which the signal is fitted (e.g. real, complex, Fourier), the number of decay components, the number of modulation frequencies, and the inclusion of a constant signal term. It is noted that the fitting function expressed in eqn. 1 is provided in the real time domain. A more generalized form of eqn. 1 is as follows, in the complex time domain:

$$S(TE) = S_{0,collagen,1} e^{-i(2\pi f_{collagen,1} TE + \varphi_{collagen,1})} e^{-TE/T_2^*_{collagen,1}} + \ldots + \quad [1c]$$
$$S_{0,collagen,m} e^{-i(2\pi f_{collagen,m} TE + \varphi_{collagen,m})} e^{-TE/T_2^*_{collagen,m}} +$$
$$S_{0,long,1} e^{-i(2\pi f_{long,1} TE + \varphi_{long,1})} e^{-TE/T_2^*_{long,1}} + \ldots +$$
$$S_{0,long,n} e^{-i(2\pi f_{long,n} TE + \varphi_{long,n})} e^{-TE/T_2^*_{long,n}} + S_{constant}$$

where there are "m" collagen $T_2^*$ components and "n" long $T_2^*$ components, and a constant signal term $S_{constant}$. $\varphi$ denotes the phase of the time-dependent modulation. It is noted that all $\varphi$, $f_{long}$, and $S_{constant}$ terms can be set to zero, as in the example bi-exponential model that is employed in the Examples below. In equation 1b, $\varphi$ is incorporated, as it is possible for the modulation to have a nonzero phase. $f_{long}$ is included because it is possible for there to be a modulation frequency in the long $T_2^*$ component due to lipids. This should give "m+n" total components for zero $S_{constant}$, and "m+n+1" total components for nonzero $S_{constant}$. Note that if one is only interested in the relative signal fraction, then one fitted parameter can be eliminated by normalizing the total signal to 1 (as shown in eqn. 1a). Eqn. 1c is a variation of eqn. 7, which is also expressed in the complex time domain. Accordingly, eqn. 1c is expressed as follows in the real time domain:

$$S(TE) = S_{0,collagen,1} \cos(2\pi f_{collagen,1} TE + \varphi_{collagen,1}) e^{-TE/T_2^*_{collagen,1}} + \quad [1d]$$
$$\ldots + S_{0,collagen,m} \cos(2\pi f_{collagen,m} TE + \varphi_{collagen,m}) e^{-TE/T_2^*_{collagen,m}} +$$
$$S_{0,long,1} \cos(2\pi f_{long,1} TE + \varphi_{long,1}) e^{-TE/T_2^*_{long,1}} + \ldots +$$
$$S_{0,long,n} \cos(2\pi f_{long,n} TE + \varphi_{long,n}) e^{-TE/T_2^*_{long,n}} + S_{constant}$$

This is the form of the equation used in examples for fitting signal from the real time domain, derived from magnitude images. In these examples, all $\varphi$, $f_{long}$, and $S_{constant}$ terms are set to zero.

Furthermore, eqn. 1c is as follows in the imaginary time domain:

$$S(TE) = \qquad [1e]$$
$$-i\big[S_{0,collagen,1}\sin(2\pi f_{collagen,1}TE + \varphi_{collagen,1})e^{-TE/T^*_{2\,collagen,1}} + \ldots +$$
$$S_{0,collagen,m}\sin(2\pi f_{collagen,m}TE + \varphi_{collagen,m})e^{-TE/T^*_{2\,collagen,m}} +$$
$$S_{0,long,1}\sin(2\pi f_{long,1}TE + \varphi_{long,1})e^{-TE/T^*_{2long,1}} + \ldots +$$
$$S_{0,long,n}\sin(2\pi f_{long,n}TE + \varphi_{long,n})e^{-TE/T^*_{2long,n}} + S_{constant}\big]$$

In another example implementation, fitting of the measured signal can be performed in the frequency domain, rather than in the time domain. One example consists of fitting the complex frequency spectra with the Fourier transformation of eqn. 1c. In other examples, one can obtain the real, imaginary, and magnitude components of the Fourier transformation of eqn. 1c, which can be used to fit real, imaginary, and magnitude frequency spectra, respectively.

There are multiple methods of acquiring signal characterized by a decay term and a modulation frequency that are associated with collagen. In this section, these techniques will be described, categorized as acquisitions of discrete and continuous time signals. Example acquisition methods are described, which include, but are not limited to, the number of imaging dimensions (e.g. two-dimensional vs. three-dimensional), the shape and timing of the radiofrequency pulse, the areas and timings of the gradient waveforms (if present), and the timing of the data acquisition window(s).

Example methods of acquisition involve those that enable fitting of a discrete time signal. This comprises fitting the decay of the measured signal at a plurality of TEs, wherein the first decay term is associated with collagen, an example of which is illustrated in FIG. 1. The ultra-short TE pulse sequence described in FIG. 3B involves acquiring all k-space trajectories while varying the TE.

Figure 3A:
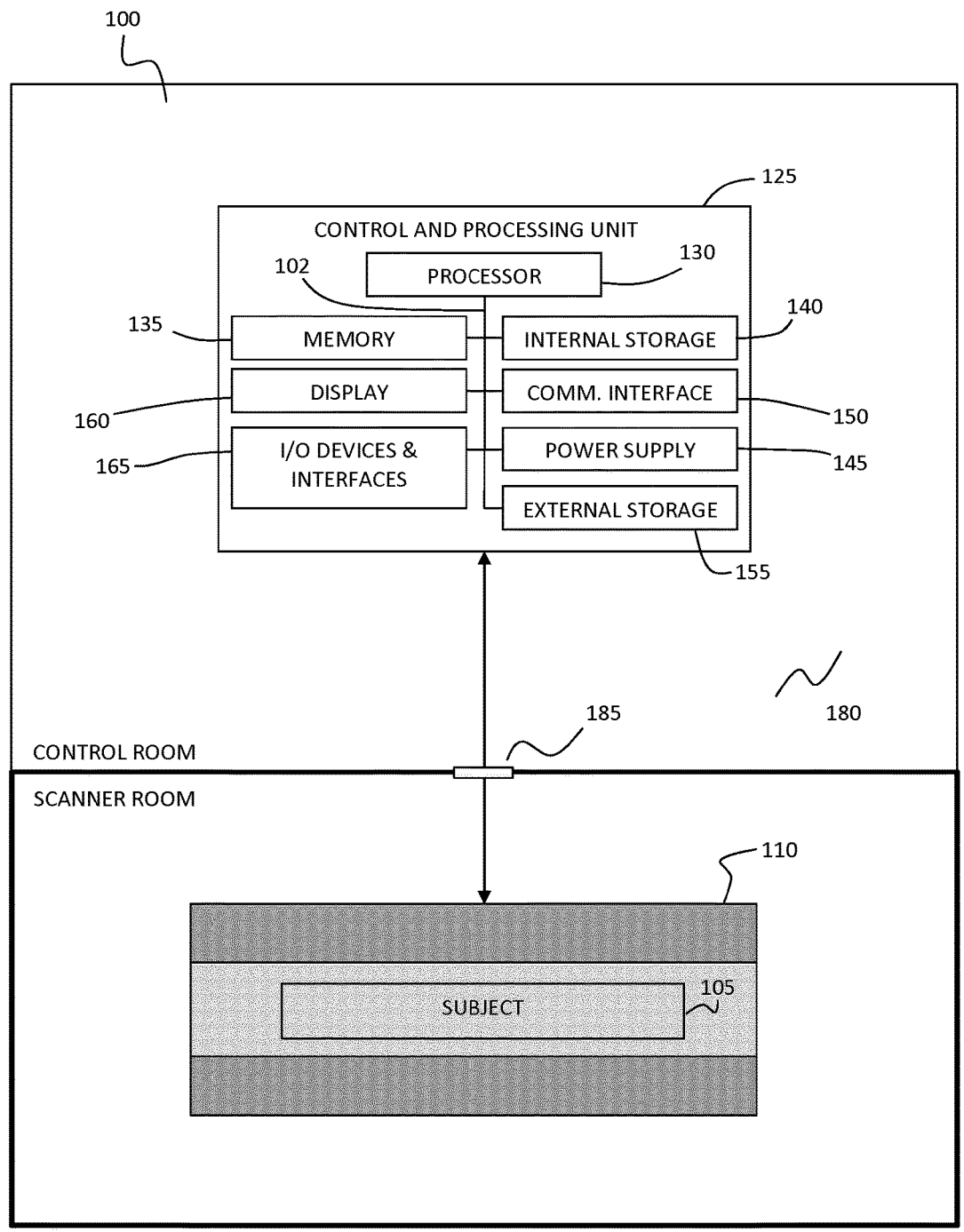
FIG. 3A shows an example magnetic resonance imaging system for detecting the presence of collagen in tissue using ultra-short TE magnetic resonance imaging.
Figure 3B:
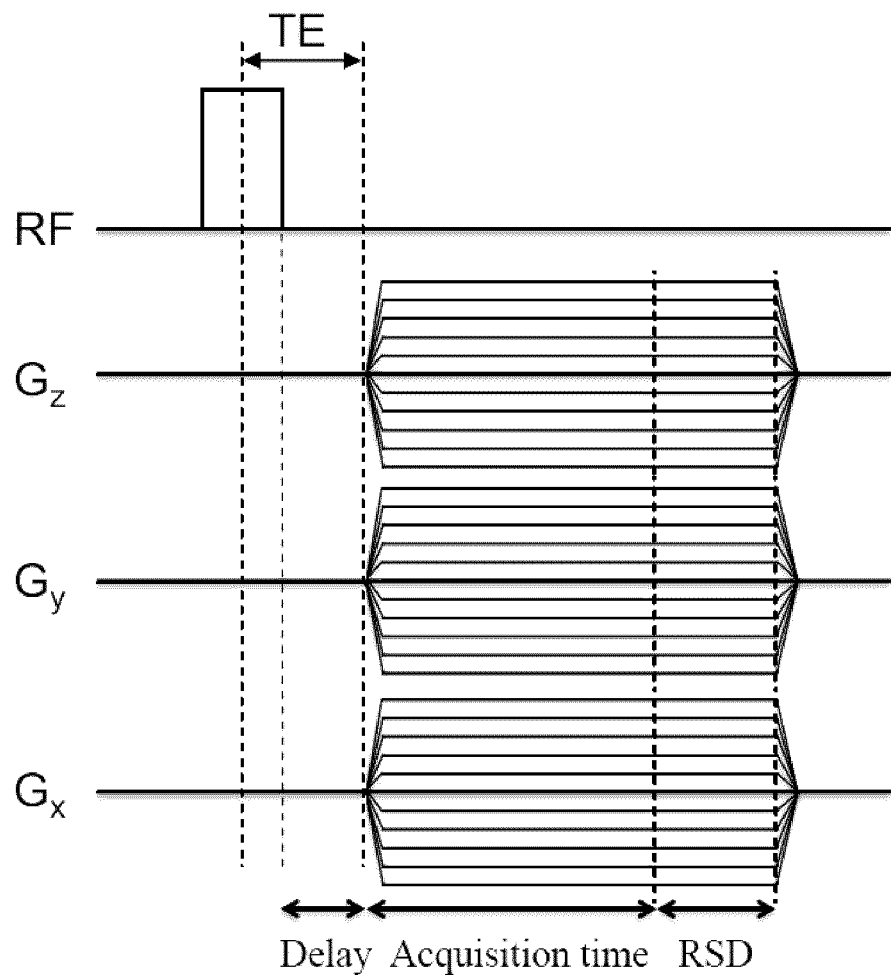
FIG. 3B shows an example 3D UTE sequence (from Bruker BioSpin). The sequence consists of a rectangular radiofrequency pulse excitation and a 3D radial acquisition. The TE is defined as the time from the middle part of the pulse to the beginning of the gradient (G) ramp-up. Different combinations of gradient amplitudes in $G_x$, $G_y$, and $G_z$ are executed to sample k-space adequately (shown in two dimensions in FIG. 3C). The hardware delay is the time needed to shift from excitation to data acquisition. The acquisition time is ~1.6 ms. RSD is the duration of the read spoiler (~1 ms), which destroys remaining magnetization in the transverse plane before the next repetition of the sequence.

In another example embodiment, the ultra-short TE pulse sequence described in FIG. 3B is modified to acquire a plurality of TEs while varying the subset of k-space trajectories. This example method is a two-dimensional pulse sequence with a half-pulse RF excitation, slice selection in the z-direction, and interleaved gradient waveforms in the x- and y-directions. The data acquisition window is turned on at discrete TEs to sample the measured signal. More detailed descriptions are found in Jiang Du et al., "Ultrashort Echo Time Spectroscopic Imaging (UTESI) of Cortical Bone," *Magnetic Resonance in Medicine* 58, no. 5 (November 2007): 1001-9, doi:10.1002/mrm.21397; Jiang Du et al., "Orientational Analysis of the Achilles Tendon and Enthesis Using an Ultrashort Echo Time Spectroscopic Imaging Sequence," *Magn. Reson. Imaging* 28, no. 2 (February 2010): 178-84, doi:10.1016/j.mri.2009.06.002; Jiang Du et al., "Ultrashort TE Spectroscopic Imaging (UTESI): Application to the Imaging of Short T2 Relaxation Tissues in the Musculoskeletal System," *Journal of Magnetic Resonance Imaging* 29, no. 2 (February 2009): 412-21, doi:10.1002/jmri.21465; Eric Diaz et al., "Ultra-short Echo Time Spectroscopic Imaging (UTESI): an Efficient Method for Quantifying Bound and Free Water," *NMR in Biomedicine* 25, no. 1 (Jul. 15, 2011): 161-68, doi:10.1002/nbm.1728.

Alternative example methods of acquisition involve fitting the free induction decay, a continuous time signal. The free induction decay may be sampled either without spatial encoding, an example being in single-voxel spectroscopy, or with spatial encoding, examples being in multi-voxel spectroscopic imaging and chemical shift imaging.

In one example implementation, a chemical shift imaging sequence is modified to achieve ultra-short TEs by reducing the time delay before each k-space point. Changing the areas of the gradient waveforms results in free induction decays with different TE weightings. This method is described in Matthew D Robson et al., "Ultra-short TE Chemical Shift Imaging (UTE-CSI)," *Magnetic Resonance in Medicine* 53, no. 2 (February 2005): 267-74, doi:10.1002/mrm.20344. Another example method, termed MR spectroscopic imaging, is described in Garry E Gold et al., "MR Spectroscopic Imaging of Collagen: Tendons and Knee Menisci," *Magnetic Resonance in Medicine* 34, no. 5 (November 1995): 647-54. Similar to UTESI, this example method is a two-dimensional pulse sequence with a half-pulse RF excitation, slice selection in the z-direction, and interleaved gradient waveforms in the x- and y-directions. However, the data acquisition window is turned on to allow for sampling of a continuous time signal.

An example method of separating materials with different modulation frequencies is by analyzing their phase difference. A modulation frequency of approximately 1 kHz attributed to collagen at 7 T signifies that collagen and water should be in phase approximately every 1 ms, and out of phase starting at approximately 0.5 ms and in intervals of approximately 1 ms. Example methods include multi-point Dixon and an iterative decomposition of water and fat with echo asymmetry and least-squares (IDEAL). In an example, multi-point Dixon is employed to obtain $T_2'$ (intravoxel susceptibility dephasing), water, fat, and $B_0$ inhomogeneity images, described in: Gary H Glover, "Multipoint Dixon Technique for Water and Fat Proton and Susceptibility Imaging," *Journal of Magnetic Resonance Imaging* 1, no. 5 (September 1991): 521-30, doi:10.1002/jmri.1880010504. $T_2'$ is derived as follows:

$$\frac{1}{T_2^*} = \frac{1}{T_2} + \frac{1}{T_2'}$$

It is noted that this method does not provide information on $T_2^*$ and, hence, is insufficient for distinguishing materials with different $T_2^*$ properties, as in collagen and cardiac muscle. In an example implementation, the multi-point Dixon approach can be extended to produce $T_2^*$ maps, while accounting for $T_2$ decay between acquisitions.

In another example embodiment, the IDEAL technique is used to process ultra-short TE images, including $T_2^*$ determination and multi-peak fat spectral modelling. From a series of ultra-short TE images, a $B_0$ inhomogeneity map and an $R_2^*$ ($=1/T_2^*$) map are generated to decompose multiple modulation frequencies. Separate images for water and the off-resonant material are generated. The example method is explained in: Kang Wang et al., "K-Space Water-Fat Decomposition with T2* Estimation and Multifrequency Fat Spectrum Modeling for Ultrashort Echo Time Imaging," *JOURNAL of Magnetic Resonance Imaging* 31, no. 4 (April 2010): 1027-34, doi:10.1002/jmri.22121. In an example implementation, this example method could be used to resolve the modulation frequencies due to collagen, and hence, produce separate images for water and collagen.

In some example implementations, the methods disclosed herein may be used to detect and optionally assess the severity of myocardial fibrosis. The decay and modulation frequency properties, when measured simultaneously, represent a unique signature of collagen that allows for collagen to be detected. The collagen signal fraction and calibration with the collagen concentration provides a measure of collagen content.

It will be understood, however, that myocardial fibrosis is but one non-limiting application, and that the methods disclosed herein may also be applied to other collagenous tissues, including, but not limited to, blocked scar, atherosclerotic plaques, chronic total occlusions, tendons, cartilage, ligaments, menisci, bone. The makeup of the collagenous tissue as well as the fitting function used will determine the collagen and long decay terms observed. In any case, the signal fraction associated with a decay term can be determined as a measure of the amount of material contributing to the decay term.

Referring now to FIG. 3A, an example magnetic resonance system is provided for performing methods disclosed herein. System 100 includes magnetic resonance imaging scanner 110, housed in a scanner room that is electromagnetically isolated by Faraday cage 180, and interfaced through patch panel 190 with control and processing unit 125, the latter of which is described in further detail below. The system shown in FIG. 3A is provided as an example system, and may include other system components, such as additional control or input device, and additional sensing devices, such as devices for cardiac and/or respiratory gating.

Control and processing unit 125 obtains magnetic resonance images of subject 105 according to an ultra-short TE pulse sequence, as described in further detail below. Control and processing unit 125 is interfaced with magnetic resonance imaging scanner 110 for receiving acquired images and for controlling the acquisition of images. Control and processing unit 125 receives image data from magnetic resonance imaging device 110 and processes the imaging data according to the methods described below.

Some aspects of the present disclosure can be embodied, at least in part, in software. That is, some methods can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's).

FIG. 3A provides an example implementation of control and processing unit 125, which includes one or more processors 130 (for example, a CPU/microprocessor), bus 102, memory 135, which may include random access memory (RAM) and/or read only memory (ROM), one or more internal storage devices 140 (e.g. a hard disk drive, compact disk drive or internal flash memory), a power supply 145, one or more communications interfaces 150, external storage 155, a display 160 and various input/output devices and/or interfaces 155 (e.g. a receiver, a transmitter, a speaker, a display, a user input device, such as a keyboard, a keypad, a mouse, a position tracked stylus, a position tracked probe, a foot switch, and/or a microphone for capturing speech commands).

Although only one of each component is illustrated in FIG. 3A, any number of each component can be included in control and processing unit 125. For example, a computer typically contains a number of different data storage media. Furthermore, although bus 102 is depicted as a single connection between all of the components, it will be appreciated that the bus 102 may represent one or more circuits, devices or communication channels which link two or more of the components. For example, in personal computers, bus 102 often includes or is a motherboard.

In one embodiment, control and processing unit 125 may be, or include, a general purpose computer or any other hardware equivalents. Control and processing unit 125 may also be implemented as one or more physical devices that are coupled to processor 130 through one of more communications channels or interfaces. For example, control and processing unit 125 can be implemented using application specific integrated circuits (ASIC). Alternatively, control and processing unit 125 can be implemented as a combination of hardware and software, where the software is loaded into the processor from the memory or over a network connection.

Control and processing unit 125 may be programmed with a set of instructions which when executed in the processor causes the system to perform one or more methods described in the disclosure. Control and processing unit 125 may include many more or less components than those shown.

While some embodiments have been described in the context of fully functioning computers and computer systems, those skilled in the art will appreciate that various embodiments are capable of being distributed as a program product in a variety of forms and are capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like.

As noted above, methods disclosed herein employ ultra-short TE imaging for detection of the short $T_2^*$ decay of collagen protons in tissue samples. It will be understood that any suitable ultra-short TE method may be employed, such as the methods described in: Sanne de Jong et al., "Direct Detection of Myocardial Fibrosis by MRI," *Journal of*

Molecular and Cellular Cardiology 51, no. 6 (December 2011): 974-79, doi:10.1016/j.yjmcc.2011.08.024; Bastiaan J van Nierop et al., "In Vivo Ultra Short TE (UTE) MRI Detects Diffuse Fibrosis in Hypertrophic Mouse Hearts," *Proceedings of the International Society of Magnetic Resonance in Medicine*, Apr. 20, 2013, 1-1; Bastiaan J van Nierop et al., "In Vivo Ultra Short TE (UTE) MRI of Mouse Myocardial Infarction," *Proceedings of the International Society of Magnetic Resonance in Medicine*, May 5, 2012, 1-1; Matthew D Robson and Graeme M Bydder, "Clinical Ultra-short Echo Time Imaging of Bone and Other Connective Tissues," *NMR in Biomedicine* 19, no. 7 (2006): 765-80, doi:10.1002/nbm.1100; Matthew D Robson et al., "Magnetic Resonance: an Introduction to Ultra-short TE (UTE) Imaging.," *Journal of Computer Assisted Tomography* 27, no. 6 (November 2003): 825-46; Matthew D Robson, Damian J Tyler, and Stefan Neubauer, "Ultra-short TE Chemical Shift Imaging (UTE-CSI)," *Magnetic Resonance in Medicine* 53, no. 2 (February 2005): 267-74, doi:10.1002/mrm.20344; Jiang Du and Graeme M Bydder, "Qualitative and Quantitative Ultra-short-TE MRI of Cortical Bone," *NMR in Biomedicine* 26, no. 5 (May 2013): 489-506, doi:10.1002/nbm.2906; Eric Diaz et al., "Ultra-short Echo Time Spectroscopic Imaging (UTESI): an Efficient Method for Quantifying Bound and Free Water," *NMR in Biomedicine* 25, no. 1 (Jul. 15, 2011): 161-68, doi:10.1002/nbm.1728; Peder E Z Larson et al., "Designing Long-T2 Suppression Pulses for Ultra-short Echo Time Imaging," *Magnetic Resonance in Medicine* 56, no. 1 (2006): 94-103, doi:10.1002/mrm.20926; Peder E Z Larson et al., "Using Adiabatic Inversion Pulses for Long-T2 Suppression in Ultra-short Echo Time (UTE) Imaging," *Magnetic Resonance in Medicine* 58, no. 5 (2007): 952-61, doi:10.1002/mrm.21341; Verena Hoerr et al., "Cardiac-Respiratory Self-Gated Cine Ultra-Short Echo Time (UTE) Cardiovascular Magnetic Resonance for Assessment of Functional Cardiac Parameters at High Magnetic Fields," *Journal of Cardiovascular Magnetic Resonance: Official Journal of the Society for Cardiovascular Magnetic Resonance* 15, no. 1 (Jul. 4, 2013): 59, doi:10.1186/1532-429X-15-59; Abdallah G Motaal et al., "Functional Imaging of Murine Hearts Using Accelerated Self-Gated UTE Cine MRI," *The International Journal of Cardiovascular Imaging*, Sep. 10, 2014, doi: 10.1007/s10554-014-0531-8.

FIG. 3B shows a non-limiting example of a 3D UTE sequence (from Bruker BioSpin). The sequence consists of a rectangular radiofrequency pulse excitation and a 3D radial acquisition. The TE is defined as the time from the middle part of the pulse to the beginning of the gradient (G) ramp-up. Different combinations of gradient amplitudes in $G_x$, $G_y$, and $G_z$ are executed to sample k-space adequately (shown in FIG. 3C).

Minimal TEs are achieved via a rectangular radiofrequency pulse of short duration (~0.02 ms) and a small delay (~0.008 ms) required to switch between the radiofrequency excitation and data acquisition. At the beginning of data acquisition, linear gradients in each spatial dimension ($G_x$, $G_y$, $G_z$) are turned on to allow for spatial localization of the imaged sample. The precession frequency of a proton (in rad/s) is, hence, a function of its location:

$$\omega(i) = \gamma B_{total} = \gamma(B_0 + G_i i) = \omega_0 + \gamma G_i i,$$

for dimensions i=x, y, z. The hardware delay is the time needed to shift from excitation to data acquisition. The acquisition time is ~1.6 ms. RSD is the duration of the read spoiler (~1 ms), which destroys remaining magnetization in the transverse plane before the next repetition of the sequence.

Figure 3C:
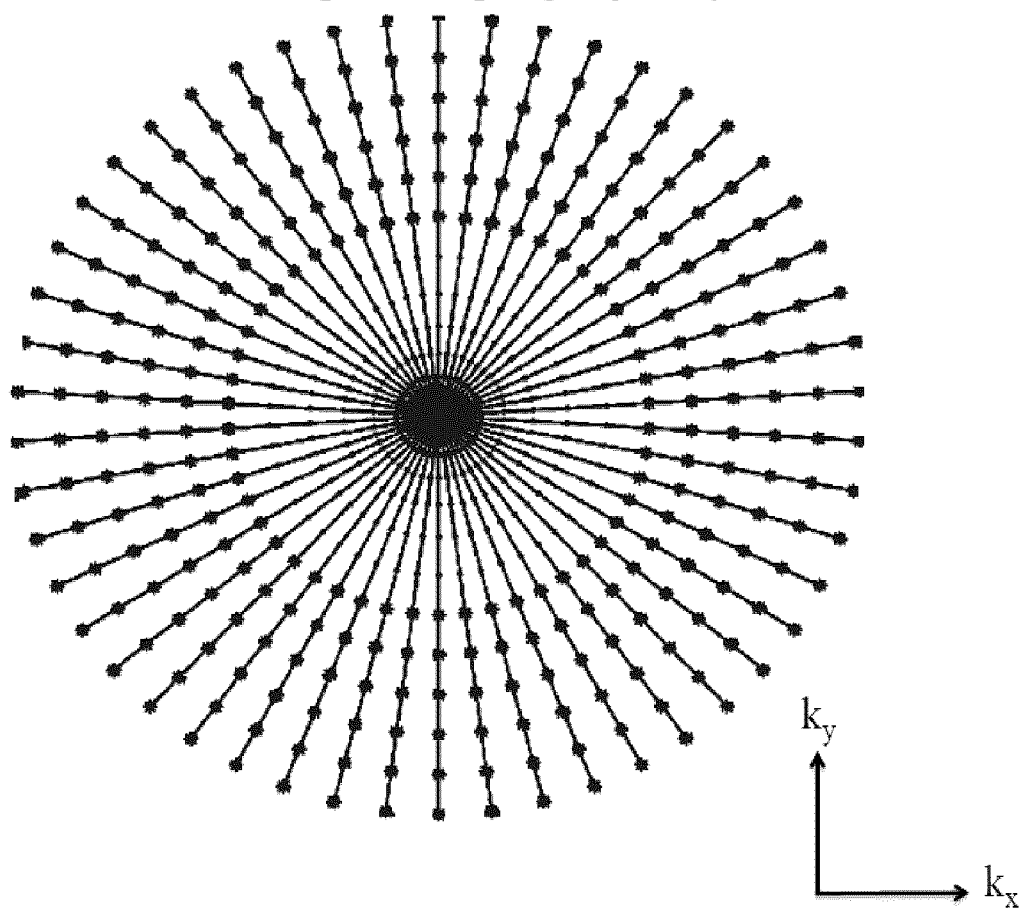
FIG. 3C illustrates the radial sampling trajectory used in UTE (2D view). Each spoke begins at the centre of k-space, and characterizes a k-space trajectory, formed by a combination of gradient waveform amplitudes. For instance, spokes in the upper right quadrant (with positive $k_x$ and $k_y$) represent cases when both $G_x$ and $G_y$ are positive. On each spoke, the dots near the centre of k-space characterize the points that are sampled on the gradient ramp, whereas the stars represent the points that are sampled on the gradient plateau.

The radial sampling trajectory used in ultra-short TE (2D view) is illustrated in FIG. 3C. Each spoke begins at the centre of k-space, and characterizes a k-space trajectory, formed by a combination of gradient waveform amplitudes. For instance, spokes in the upper right quadrant (with positive $k_x$ and $k_y$) represent cases when both $G_x$ and $G_y$ are positive. On each spoke, the dots near the centre of k-space characterize the points that are sampled on the gradient ramp, whereas the stars represent the points that are sampled on the gradient plateau.

The coordinates $k_x$, $k_y$, and $k_z$ are proportional to the areas under the gradient waveforms $G_x$, $G_y$, and $G_z$:

$$k_i(t) = \frac{\gamma}{2\pi} \int_0^t G_i(\tau) d\tau.$$

Each spoke in the trajectory is achieved by varying the amplitudes of the gradient waveforms, allowing for sampling of all quadrants of k-space. For image reconstruction, the sampled points are regridded in Cartesian coordinates, before an inverse Fourier transform is applied. For each TE, the UTE pulse sequence would be repeated with the same imaging parameters, with the exception of the TE. By sampling the MR signal over a range of TEs, the T2* of the imaged sample may be characterized.

However, if the T2* of the sample is less than the acquisition time of ~1.6 ms, then there will be significant T2* decay during the readout. As a result, the signal at high spatial frequencies will be attenuated, causing a loss of spatial resolution. It is for this reason that MR images of short T2* species are blurred, indicating the usefulness of T2* signal analysis over assessment of image contrast from short T2* species.

Considerations for Clinical Implementations

It is noted that in the examples provided below, the resonance frequency (approximately 1.1 kHz upfield of water) and $T_2$* of collagen protons (approximately 0.8 ms) at 7 T were measured in a detailed manner that would not be feasible in a clinical setting, due to the long scan times (>11 hours). The application of the methods disclosed herein to UTE MRI in a clinical context would involve sampling with fewer TEs, in order to complete the patient examination in a reasonable amount of time. The optimal sampling scheme would involve sampling the fewest number of points without sacrificing crucial signal information, particularly the resonance frequency.

On the 7-T system described in the Examples sections, a collagen $T_2$* of approximately 0.8 ms and a collagen resonance frequency of approximately 1.1 kHz were determined. According to the Nyquist sampling theorem, in order to characterize a 1 kHz frequency, the lowest sampling interval required would be 0.5 ms. In order to sample the collagen resonance frequency of 1.1 kHz within a reasonable examination time, one could acquire the data according to the following example TEs: 0.02 (or the minimum TE available), 0.5, 1, 1.5, 2, 2.5, 3, 5, 10, 15, 25 ms (values are approximate).

When performing fitting using the two-step embodiment described above involving an initial T2* fitting step, the collagen T2* may be fixed to 0.8 ms, and the collagen resonance frequency may be fixed to 1.1 kHz, in order to increase the fitting accuracy. For example, in the 0% to 50% collagen solutions employed in the Examples that are described below, this strategy yielded similar collagen signal fractions to those obtained with the original high TE sampling density scheme, suggesting the validity of this approach.

From the fit, the collagen signal fraction would then be determined, which could then be employed to quantify the amount of collagen by relating the signal fraction to the collagen concentration via a calibration plot, are described above.

Figure 3D:
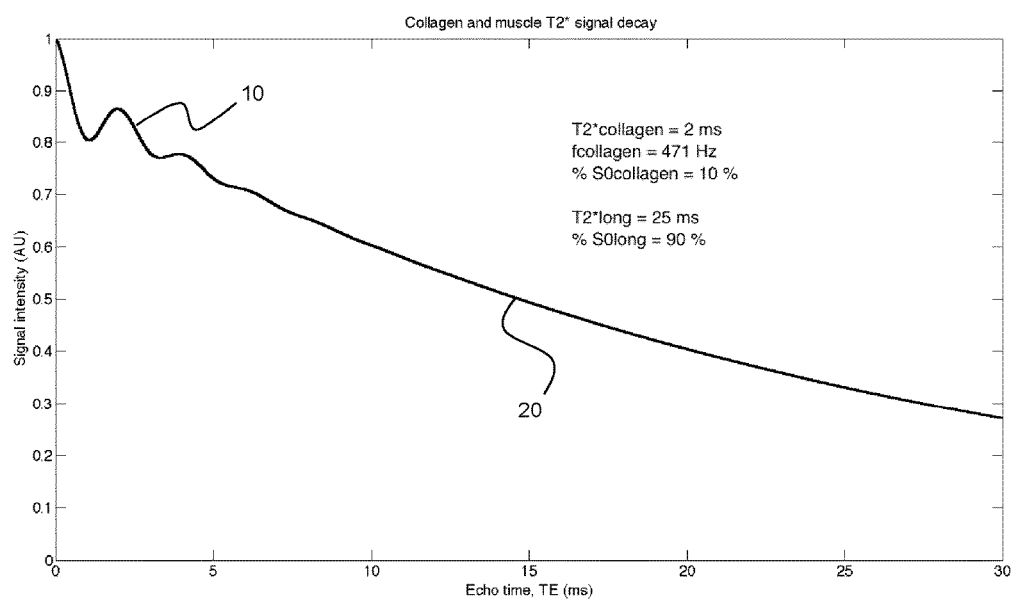
FIG. 3D plots the simulated TE dependence for the imaging of collagen-containing tissue using ultra-short TE imaging for a 3 T system, illustrating the bi-exponential nature of the signal, and the modulated decay component attributed to collagen protons.

Further considerations for clinical implementation include the changes in collagen resonance frequency and $T_2^*$ associated with lower magnetic field strengths, e.g. at 1.5 T and 3 T, as well as pulse sequence modifications for in vivo imaging. Specifically, a resonance frequency of approximately 1 kHz at 7 T would decrease to approximately 429 Hz at 3 T, and 214 Hz at 1.5 T. On a 3-T clinical system, one would expect a collagen T2* of approximately 0.5 to 3.0 ms. Without intending to be limited by theory, if the T2* is influenced by chemical shift dispersion, then the T2* value should increase slightly with decreasing magnetic field strength. Otherwise, if the T2* is not due to chemical shift dispersion, then the T2* should be approximately the same at a lower field strength. FIG. 3D plots the simulated TE dependence for the imaging of collagen-containing tissue using ultra-short TE imaging for a 3 T system, illustrating the bi-exponential nature of the signal, and the modulated decay component attributed to collagen protons.

The collagen resonance frequency decreases proportionally with decreasing magnetic field strength, and the collagen resonance frequency would be expected to be approximately 471 Hz for a 3 T system. Given the resonance frequency, this would correspond to a period of approximately 2 ms. Hence, the MR signal should be out of phase starting at approximately 1 ms and in intervals of approximately 2 ms; the signal should be in phase approximately every 2 ms.

As noted above, the TEs should be sampled at a sufficiently high density to determine the resonance frequency. Thus, in one example implementation, the following approximate TEs could be acquired: 0.02 (the minimum TE), 1, 2, 3, 4, 5, 10, 15, 25 ms. The few TEs acquired would cause the collagen signal fraction to have higher uncertainty; to remedy this, one could perform an initial T2* fitting over the modulation region and decrease the number of fitting parameters for a subsequent global fitting step by fixing the values of the collagen T2* and the resonance frequency.

As noted above, in one example embodiment involving analysis over an entire patient's heart, one could average the signal intensities over either a volumetric ROI or an ROI of a thick slice. The ROI used for T2* analysis would ideally cover the expected region of fibrosis, e.g. the left ventricle, while excluding regions with interfering signals such as the blood pool.

Modifications to the UTE sequence would be required for in vivo implementation, including, but not limited to, cardiac and respiratory gating, as well as accelerated acquisition strategies. Several in vivo UTE sequences have been reported for cardiac murine imaging, employing example strategies such as electrocardiogram-triggered respiratory gating [13], [14], cardiac-respiratory self-gated cine [26], and accelerated cardiac-respiratory self-gated cine [27]. Notably, Motaal et al. [27] acquired UTE cine images while undersampling k-space by up to five times, resulting in acquisitions times as low as 15 s; a compressed sensing algorithm was used for image reconstruction.

It will be understood that any method of reducing motion artifacts may be employed. For example, self-gating could be employed to avoid or reduce motion artifacts. Self-gating is a retrospective gating method that uses a navigator (the first data point of the acquisition) to acquire information on cardiac and respiratory motion. Alternatively, electrocardiogram-triggered respiratory gating could be employed to reduce motion artifacts.

For in vivo acquisition, one example implementation would involve acquiring one MRI slice in the patient's heart. In this manner, undersampling of the MR signal in Fourier (k-) space may not be necessary. Otherwise, if many MRI slices are acquired, random undersampling in k-space may be employed; where reconstruction of the images would involve a compressed sensing algorithm. Examples of compressed sensing algorithms include: Michael Lustig, David Donoho, and John M Pauly, "Sparse MRI: the Application of Compressed Sensing for Rapid MR Imaging," *Magnetic Resonance in Medicine* 58, no. 6 (2007): 1182-95, doi: 10.1002/mrm.21391; and Abdallah G Motaal et al., "Functional Imaging of Murine Hearts Using Accelerated Self-Gated UTE Cine MRI," *The International Journal of Cardiovascular Imaging*, Sep. 10, 2014, doi:10.1007/s10554-014-0531-8.

Although the preceding example embodiments have pertained to the detection of signals associated with collagen protons, it is to be understood there are multiple additional nuclei for which the signal can be characterized by a decay term and a modulation frequency that are associated with collagen. Example nuclei include, but are not limited to, $^{13}C$ and $^{15}N$; one may detect signal from labelled nuclei associated with collagen, or signal from naturally abundant nuclei associated with collagen. Example acquisition methods include $^{13}C$ spectroscopy, described in: Detlef Reichert et al., "A Solid-State NMR Study of the Fast and Slow Dynamics of Collagen Fibrils at Varying Hydration Levels," *Magnetic Resonance in Chemistry* 42, no. 2 (Jan. 16, 2004): 276-84, doi:10.1002/mrc.1334; S K Sarkar, C E Sullivan, and D A Torchia, "Solid State 13C NMR Study of Collagen Molecular Dynamics in Hard and Soft Tissues," *The Journal of Biological Chemistry* 258, no. 16 (Aug. 25, 1983): 9762-67; L Naji et al., "13C NMR Relaxation Studies on Cartilage and Cartilage Components," *Carbohydrate Research* 327, no. 4 (Aug. 7, 2000): 439-46. An example acquisition method for $^{15}N$ spectroscopy is described in: Akira Naito, Satoru Tuzi, and Hazime Saito, "A High-Resolution 15N Solid-State NMR Study of Collagen and Related Polypeptides. the Effect of Hydration on Formation of Interchain Hydrogen Bonds as the Primary Source of Stability of the Collagen-Type Triple Helix," *European Journal of Biochemistry* 224, no. 2 (September 1994): 729-34, doi:10.1111/j.1432-1033.1994.00729.x. Spectroscopy of collagen demonstrates that at least one modulation frequency of collagen may be detected, depending on the reference nucleus. It is understood that one may determine a decay term and modulation frequency associated with collagen for a nucleus of interest, assuming that sampling of the measured time signal is sufficient for such purposes.

The following examples are presented to enable those skilled in the art to understand and to practice embodiments of the present disclosure. They should not be considered as a limitation on the scope of the disclosure, but merely as being illustrative and representative thereof.

EXAMPLES

Example 1: Measurement of UTE Signal Decay in Reference Collagen Solutions

In order to validate Eq. 1 in a controlled environment, collagen solutions of varying concentrations were prepared and analyzed with UTE MRI. The collagen solutions were prepared by dissolving hydrolyzed type I and III collagen powder (NeoCell Super Collagen Type I and III Powder, NeoCell, Irvine, Calif., USA) in 0.125 mM manganese chloride ($MnCl_2$) solvent. Types I and III were employed because they are the most abundant collagen types in the heart [20]. Pharmaceutical food grade bovine hide collagen was the source of the powder. The manganese chloride solution was prepared by dissolving the appropriate amount of manganese(II) chloride tetrahydrate ($MnCl_2.4H_2O$) (ReagentPlus grade, Sigma-Aldrich, Oakville, Ontario, Canada) in Milli-Q water (EMD Millipore, Billerica, Mass., USA). This $MnCl_2$ solution approximated the long $T_2^*$ of cardiac muscle, valued at ~35 ms [21]. Concentrations, expressed as % mass/volume (% m/v), were as follows: 0%, 2.5%, 5%, 10%, 20%, 30%, 40%, 50%. At 50% m/v concentration, i.e. with 50 g of collagen dissolved in a solution with total volume of 100 mL, the solution approached the saturation point for collagen solubility; hence, higher concentrations were not prepared. For scanning, the solutions were placed in 5-mL glass tubes.

Example 2: Preparation of Heart Tissue Samples

For investigation of the myocardial fibrosis $T_2^*$ model in the heart, ex vivo canine heart tissue afflicted with diffuse myocardial fibrosis was employed. Animal procedures were approved by the Animal Care Committee of St. Michael's Hospital (Toronto, ON, Canada). A bipolar IS-1 pacemaker (Model 5156 Verity ADx XL SR, St. Jude Medical Minneapolis, Minn., USA) was implanted into one mongrel dog aged 1-2 years, weighing 20-30 kg. After a one-week recovery period, simultaneous atrioventricular pacing at 220 bpm was induced for 14 days, by adjusting the pacemaker to VVI mode at 220 bpm, with a pulse width of 1 ms and a pulse amplitude of 5.0 V. At the end study, the heart was rapidly removed, while the canine was heavily anesthetized. Ex vivo left atrial appendage heart tissue was fixed in 10% neutral buffered formalin for one day at 4° C. Prior to scanning, the tissue was brought to room temperature. The sample was cut to approximately 5 mm×5 mm×5 mm in size and wedged in a 5-mm diameter, 1-mL glass tube, which was wrapped in Teflon tape to prevent motion. Magnetic susceptibility artifacts at the air-tissue interface were minimized by filling the tube with Fluorinert (3M, Saint Paul, Minn., USA). For scanning, the tube was placed inside a 1.3 cm-diameter, 5-mL glass tube and inserted into a cylindrical Teflon holder of slightly larger diameter; the holder contained a locally made radiofrequency surface coil.

Example 3: MR Measurements

Experiments were performed on a 7-T horizontal-bore Bruker BioSpec 70/30 scanner (Bruker BioSpin, Ettlingen, Germany), using ParaVision 5.1 software. The system had a gradient amplitude of 200 mT/m and a maximum slew rate of 640 T/m/s [23]. A 4.8 cm×1.5 cm locally built surface radiofrequency coil was utilized for transmitting and receiving signal.

For UTE measurements of the collagen solutions and heart tissue, a 3D UTE Bruker stock pulse sequence was employed, characterized by radial sampling and a non-selective rectangular radiofrequency pulse of length 0.02 ms. A delay of 0.004 ms was required to switch from radiofrequency excitation to data acquisition. To begin at the centre of k-space, sampling was executed on the gradient ramp. The acquisition time was 1.6 ms; this was followed by a spoiler in the readout direction for 1 ms, to remove spurious signals before the next repetition time.

Scans were conducted at a temperature of 21±2° C. Imaging parameters are summarized in FIG. 4. For the collagen solutions, the decay curve was sampled at high TE density, particularly within the initial 5 ms to facilitate proper identification of important chemical shift and $T_2^*$ decay components. Images were reconstructed on the Bruker workstation, involving regridding of raw data to Cartesian coordinates followed by an inverse Fourier transformation.

A non-localized spectroscopy (NSPECT) stock pulse sequence from Bruker was executed for obtaining an MR spectrum of the 50% collagen solution. This was acquired for comparison with the collagen spectrum of Kaflak-Hachulska et al. [17]. A 90°-rectangular pulse lasting 0.007 ms, followed by an acquisition delay of 0.05 ms, and a free induction decay acquisition of 262.14 ms characterized the NSPECT sequence. The spectroscopy parameters are outlined in FIG. 5.

Example 5: Analysis of Collagen Solutions

UTE magnitude images reconstructed from the Bruker workstation were used for analysis, in order to minimize phase artifacts; in order to demonstrate images compatible for clinical implementation, the same type of images as those used in the clinic were selected. Region-of-interest (ROI) selection and data fitting were performed in MATLAB R2012a (The MathWorks, Natick, Mass., USA).

For each collagen solution, a 10-×8-pixel ROI was selected over an axial slice at the tube's centre; this was done to minimize the contributions of artifacts due to magnetic susceptibility, phase differences, and Gibbs' ringing. Pixels in the ROI were averaged to obtain the mean signal intensity as a function of TE. $T_2^*$ fitting of Equation [1] over the ROI was conducted via a trust-region-reflective nonlinear least-squares algorithm in MATLAB. This amounted to a five-parameter fit, with the loose constraints specified in FIG. 6. It is noted that the full TE range was fitted in a single step.

Uncertainties in the fit parameters of eqn. 1 were calculated as standard errors (standard deviations), determined from the accuracy of the fit. Consider a nonlinear least-squares fit, yielding residual $r_i$ for the $i^{th}$ data point and fit parameter $\beta_j$ for the $j^{th}$ parameter. The Jacobian matrix J has entries $J_{ij}$, defined as follows:

$$J_{ij} = \frac{\partial r_i}{\partial \beta_j} \quad [3]$$

The mean squared error (MSE) can be calculated from the sum of the squared 2-norms of the residuals and the degrees of freedom v:

$$MSE = \frac{\sum_i \|r_i\|^2}{v} \quad [4]$$

Assuming that J is non-singular (invertible), one can determine the covariance matrix (COV), based on J and MSE:

$$COV = (J^T J)^{-1} \cdot MSE \quad [5]$$

The standard errors are the standard deviations of the fit parameters, i.e. the square roots of the diagonal entries of the covariance matrix.

The collagen signal fraction determined from UTE was compared to its known concentration in a calibration plot and regression analysis, performed in Excel for Mac 2011 (Microsoft, Redmond, Wash., USA). Below is the equation for the collagen signal fraction:

$$\text{Collagen signal fraction} = \frac{S_{0,collagen}}{S_{0,collagen} + S_{0,long}} \times 100\% \quad [1a]$$

Analysis of the NSPECT spectrum of the 50% collagen solution was performed in MestReNova 9.0.1 (Mestrelab Research, Santiago de Compostela, Spain). Using the software, manual corrections for zero- and first-order phase and the baseline were achieved on the real spectrum. To compare the NSPECT and UTE analyses, a frequency spectrum was generated using the complex form of Equation [1]:

$$S(TE) = S_{0,collagen} e^{-i2\pi f_{collagen} TE} e^{-TE/T_2^*_{collagen}} + S_{0,long} e^{-TE/T_2^*_{long}} \quad [7]$$

where the parameter values acquired from fitting eqn. 1 were substituted (see FIG. 9 for the exact values for the 50% solution). The Fourier transformation of the above equation was taken, and its real part was produced as a spectrum. Eqn. 7 was used to generate the real spectrum; by contrast, the original eqn. 1 was fit with magnitude data, which would give rise to a symmetric spectrum upon Fourier transformation.

Example 6: Analysis of Heart Tissue

Histological processing and analysis were performed to compare histological and UTE MR images. The 5 mm×5 mm×5 mm formalin-fixed heart sample was embedded in paraffin. Five histological sections were taken from the middle of the sample, where each section was separated by ~300 μm and had a thickness of 4 μm. Each section was removed of paraffin, hydrated, and stained with Hematoxylin (for nuclei), followed by Picrosirius Red (for collagen). Following washes in acidified water, each section was dehydrated in ethanol and xylene, before being mounted on a microscope slide [24].

Each slide was processed with a Leica SCN400 F brightfield scanner (Leica Biosystems, Vista, Calif., USA) at a magnification of 20×. The histological images were analyzed using Aperio ImageScope 11.2 (Leica Biosystems, Vista, Calif., USA). A 781.2 μm×781.2 μm (5-×5-pixel) ROI was extracted from each of the five sections, avoiding sample edges and voids due to tissue processing.

Using code written in MATLAB, dark nuclei were selected from the red channel of the ROI using a pixel threshold. These nuclei were removed from all colour channels of the image via conversion to white pixels. If needed, large areas with particle contamination were subsequently removed from the image by manual segmentation in ImageJ 1.46r (National Institutes of Health, Bethesda, Md., USA). A pixel threshold algorithm from ImageJ was used to select for the red (i.e. collagen) pixels. For each ROI, the collagen area fraction was quantified as the percentage of red pixels out of all pixels in the image. To determine the uncertainty in the collagen area fraction, two pixel thresholds were chosen by visual inspection: (1) a low threshold denoting a 2% collagen area fraction, the lower limit for inclusion of collagen pixels, and (2) a high threshold denoting a 6% collagen area fraction, the upper limit at which non-collagen pixels were included in the estimate. For each of the five ROIs, the collagen area fraction was evaluated to be 4±2%, referring to a middle pixel threshold with the uncertainty specifying the range of collagen area fractions achieved from the low to high thresholds. There was, hence, little variation in collagen area fraction across the ROIs.

For each ROI, the UTE MRI slice that best aligned with the histological image was chosen, when the sample edges were compared by visual inspection. Both histological and MR images were cropped along their edges and resized to square matrices in MATLAB. With both images aligned side-by-side on gridded coordinates, the ROI from histology was reproduced on the MR image. It is noted that a large ROI lessened potential error contributions due to image artifacts, alignment discrepancies, and changes in tissue shape.

To obtain accurate values of the Eq. 1 fit parameters, MR ROI analysis in the heart tissue was conducted as a two-step process, in lieu of the one-step procedure used when analyzing the collagen solutions: (1) first by fitting the mean signal intensities at finely sampled TEs ranging from 0.02 ms to 2 ms; then (2) by fitting the full range of TEs from 0.02 ms to 25 ms, with the upper limit of $T_2^*_{collagen}$ fixed according to the $T_2^*_{collagen}$ from (1). Emphasizing the short TE range via the separated fitting method ensured that the short TEs were fitted, as the nonlinear least-squares algorithm was not compensating for the sparsely sampled long component at the expense of the finely sampled short component; this was an improvement over fitting the full range of TEs without fixing parameters. All unfixed parameters were given the loose constraints outlined in FIG. 6.

Example 7: Results from Analysis of Collagen Solutions

Figure 7A:
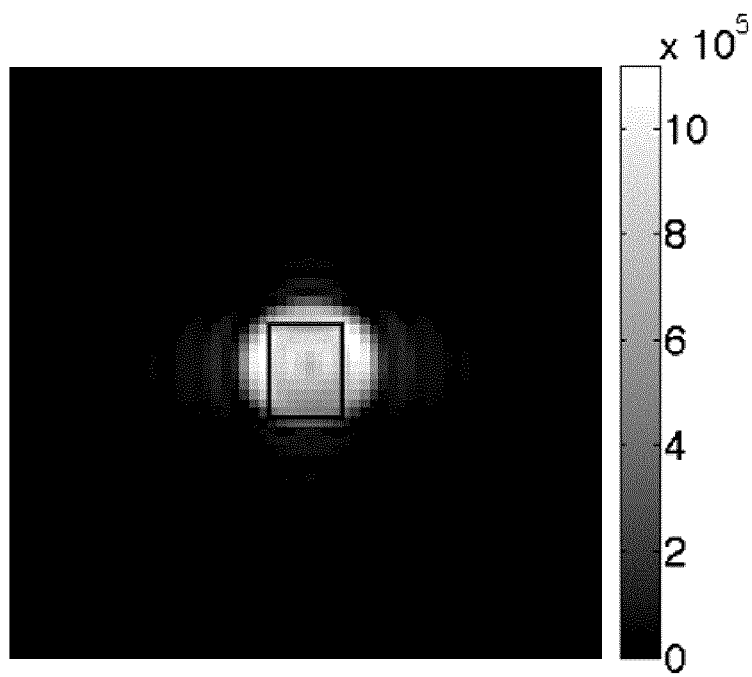
FIGS. 7A and 7B show results from the analysis of a 50% collagen solution.
Figure 7B:
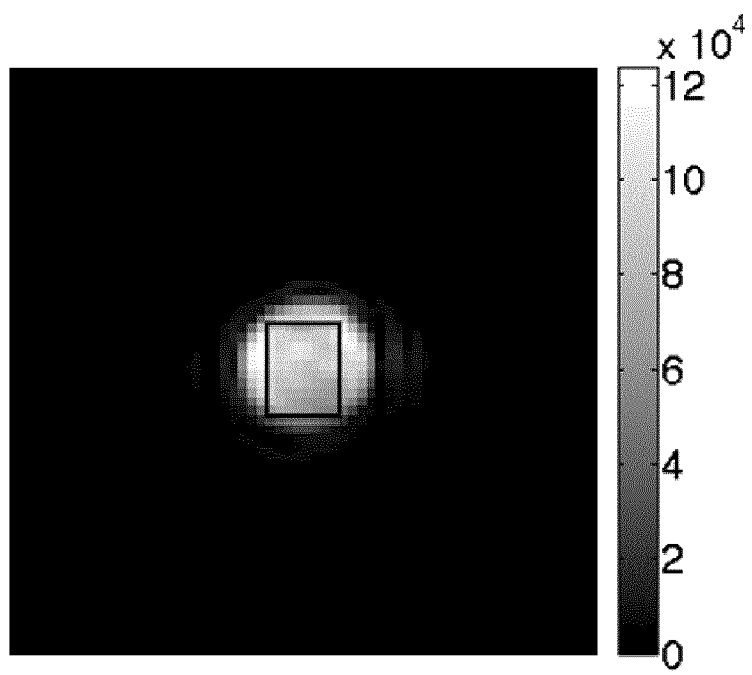

The $T_2^*$ decays of the collagen solutions were analyzed, and the resulting collagen signal fractions were compared with their concentrations. FIGS. 7A and 7B are axial UTE images of a 50% collagen solution at the shortest TE of 0.02 ms and the longest TE of 25 ms. The rectangles outline the 10-×8-pixel ROI over which the pixel signal intensities were averaged. FIG. 1A illustrates the resulting $T_2^*$ decay of the 50% collagen solution, where each point represents the average signal intensity over the ROI for a given TE. The short TE range of 0.02 ms to 5 ms was finely sampled to allow for characterization of $T_2^*_{collagen}$, which was 0.71±0.07 ms and contributed to 20±1% of the signal. Oscillation of the collagen signal was characterized by a frequency of 1.06±0.02 kHz. By contrast, $T_2^*_{long}$ was 11.3±0.2 ms. The uncertainties represent the standard errors in the least-squares fit.

Figure 8:
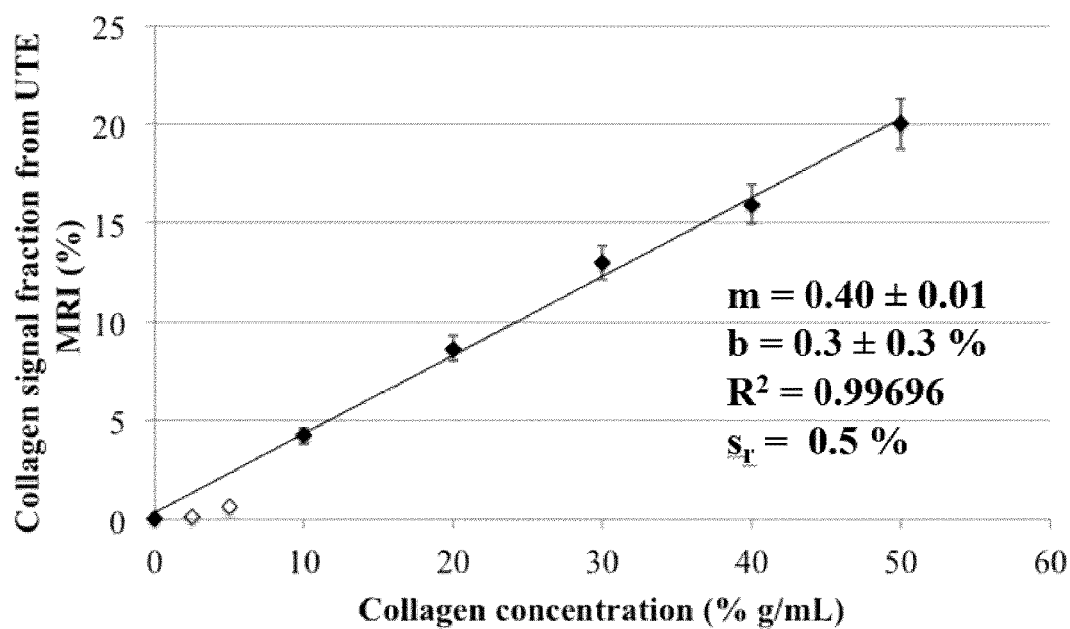
FIG. 8 is a calibration plot obtained relating the collagen signal fraction (based on UTE measurements) to the collagen concentration of calibration collagen solutions. The error bars for the collagen signal fractions were derived from the propagation of standard errors in $S_{0,collagen}$ and $S_{0,long}$. The black points were included in the linear regression; the white points were excluded due to large or undetermined standard errors in $S_{0,collagen}$ and $S_{0,long}$, resulting in underestimation of the collagen signal fraction. Values of the slope (m), y-intercept (b), correlation coefficient ($R^2$), and standard deviation about the regression ($s_r$) are given.

FIG. 8 is a calibration plot showing the linear relationship between the collagen concentration in % g/mL (horizontal axis) and the collagen signal fraction in % from UTE MRI (vertical axis). The error bars are the uncertainties in the collagen signal fraction, obtained from the error propagation of standard errors in $S_{0,collagen}$ and $S_{0,long}$ (refer to eqn. 1a for the calculation of the collagen signal fraction). From the linear regression analysis, the slope (m) and intercept (b) were 0.40±0.01 and 0.3±0.3%, respectively; the correlation coefficient ($R^2$) was 0.99696. 0.5% was the standard deviation about the regression ($s_r$). It should be noted that regression analysis was performed only on the data points in black; the data points in white were excluded due to large or undetermined uncertainties in the $T_2^*$ fitting parameters, leading to underestimation of the collagen signal contribution (vide infra).

The collagen solution calibration plot establishes a linear relationship between the collagen signal fraction from UTE MRI and the known collagen concentration. A high regression value of 0.99696 was obtained, with a low standard deviation about the regression of 0.5%. Hence, the utility of the proposed $T_2^*$ model for estimating collagen was demonstrated. The fitted slope was 0.40±0.01; for instance, a 10% m/v collagen solution would produce a 4% collagen signal. Without intending to be limited by theory, it is reasonable that the slope was not equal to unity because the collagen concentration was expressed as % m/v, rather than % hydrogen nuclei in collagen/total hydrogen nuclei. In this case, the mass of collagen powder and the final volume of the solution were known, while the relative number of protons per unit mass associated with the fitted frequency was not. As expected, the 0% m/v collagen solution, which was fitted with the full model of bi-exponential $T_2^*$ with oscillation, revealed an insignificant collagen signal fraction of $1\times10^{-7}$%.

The values of the fit parameters and their standard errors for each collagen solution are displayed in FIG. 9. Values followed by an asterisk (*) could not be determined accurately, due to a Jacobian matrix of residuals that was either singular or close to singular, and resulting in an ill-defined covariance matrix (refer to eqn. 5). The primary reason for a singular Jacobian matrix was instability in the fit, apparent at collagen concentrations of 0% and 2.5%, due to a low collagen signal that was difficult to characterize. Consequently, the solutions to the least-squares fit were non-unique (linearly dependent), and could not be known exactly.

It is noted that the full bi-exponential $T_2^*$ with oscillation equation was used for fitting the 0% solution (i.e. the 0.125 mM $MnCl_2$ solution); as expected, the collagen signal contribution ($1\times10^{-7}$%) and frequency ($4\times10^{-12}$ kHz) were negligible. Due to the reduced collagen signal, the estimation of $T_2^*{}_{collagen}$ was not ideal for the 2.5% and 5% solutions, with values of $5\times10^{-3}$ ms and 3±2 ms, respectively. As a result, the collagen signal contributions for these solutions were lower than expected (0.1% and 0.6±0.3%, respectively).

It is apparent that the $T_2^*$ and frequency of collagen remained relatively constant for concentrations ranging from 10% to 50%, with means of 0.75±0.05 ms and 1.061±0.004 kHz respectively. $T_2^*{}_{long}$ ranged from 11.3 ms to 38.2 ms, and decreased with increasing collagen concentration.

As shown in FIG. 9, the example bi-exponential $T_2^*$ fitting function performed well for collagen concentrations ≥10% m/v, equivalent to ≥4% collagen signal fractions. Assuming that a collagen concentration of 10% is equivalent to a collagen area fraction of 10% in the heart, this reflects the range where myocardial fibrosis is considered significant [3], [4]; hence, accurate characterization for collagen concentrations below 10% may not be important for disease diagnosis.

At low collagen concentrations of 2.5% and 5%, the collagen signal fractions tended to be underestimated. As the collagen $T_2^*$ component was very small, the amplitude of the signal oscillation became comparable to that of noise. However, fixing parameters $T_2^*{}_{collagen}$ and/or $f_{collagen}$ to their mean values did not significantly improve the estimates of collagen signal fraction for the 2.5% and 5% collagen solutions. It appears that that underestimation of the collagen signal fraction at low collagen concentrations is an inherent limitation in the model of bi-exponential $T_2^*$ with oscillation, apparent for collagen concentrations <10%.

Figure 10A:
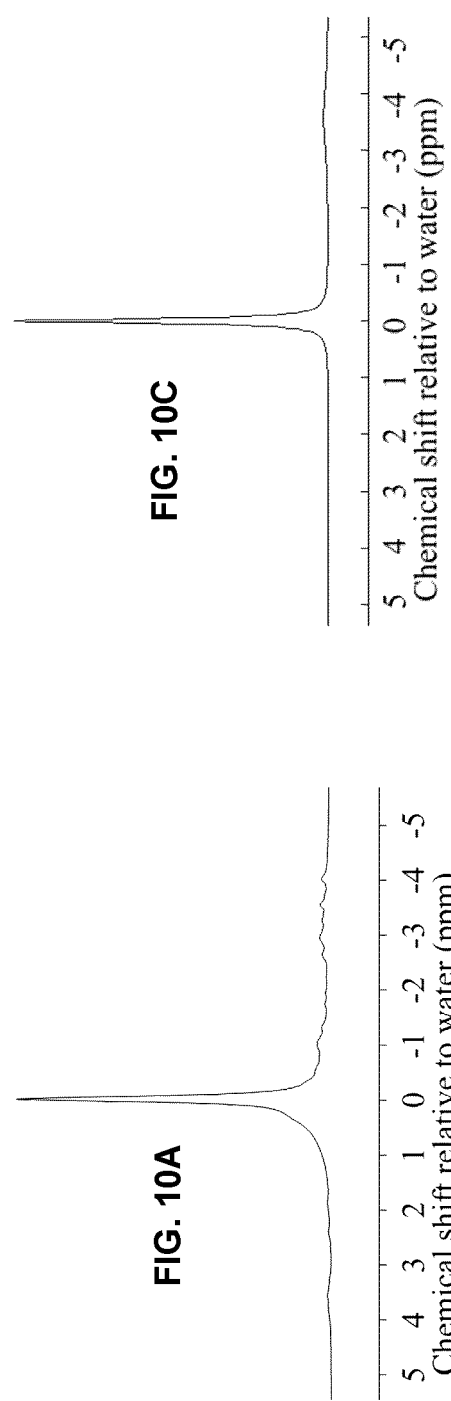
FIGS. 10A-D show several collagen MR spectra.
Figure 10C:
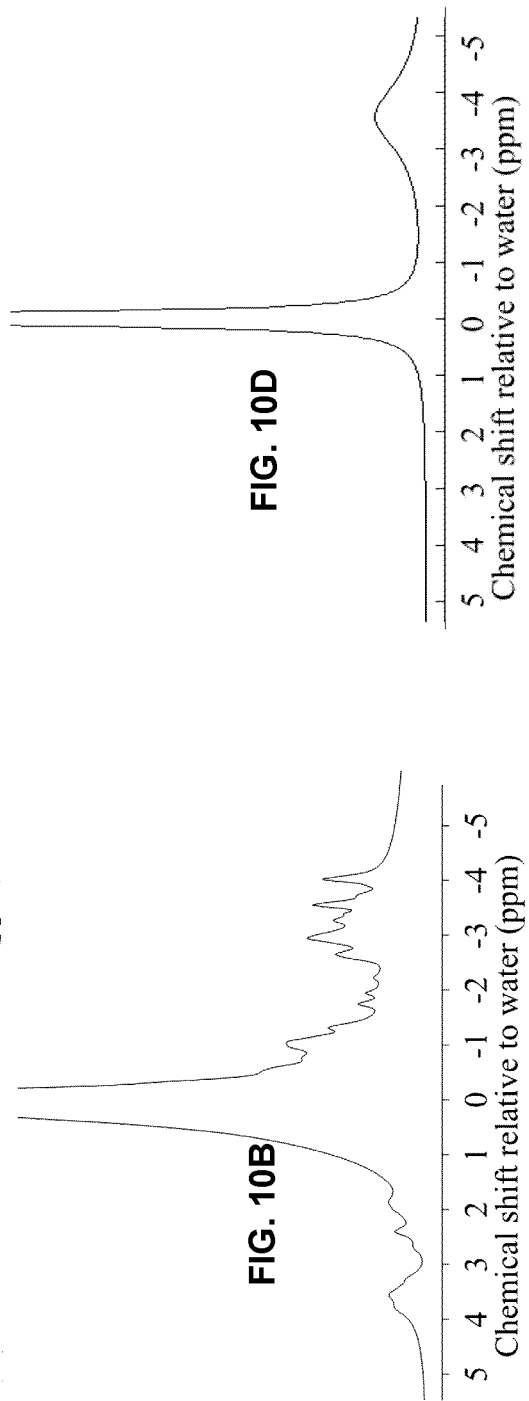
Figure 10B:
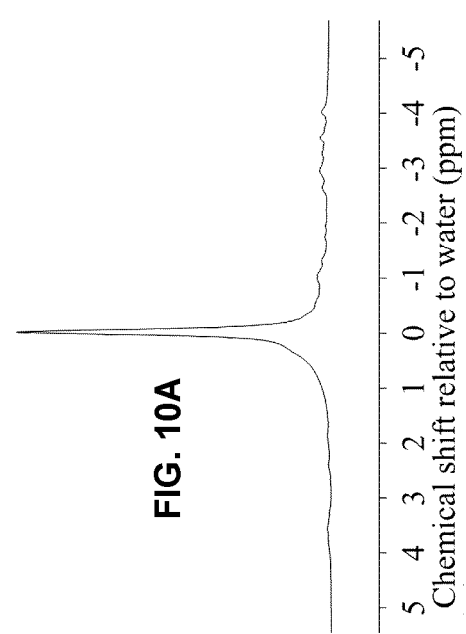
Figure 10D:
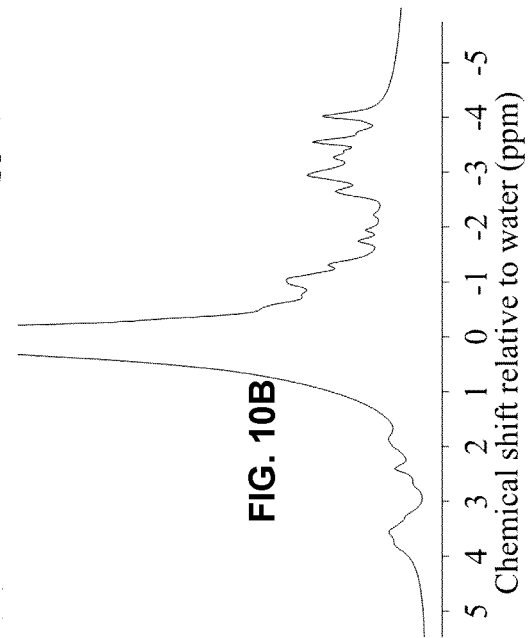

Given the high collagen signal fraction of the 50% solution, its MR spectrum was analyzed with respect to collagen characterization. FIG. 10A is the real spectrum of the 50% solution generated from NSPECT. The spectrum is enlarged in FIG. 10B. Individual collagen peaks were detected between −2.6 ppm and −4.0 ppm. The real frequency spectrum of the 50% collagen solution is shown in FIGS. 10C and 10D, produced by eqn. 7 and the parameter values associated with the fit (refer to FIG. 9). The central peak at 0 ppm was due to the long $T_2^*$ component (water). A peak due to the short $T_2^*$ component (collagen) was centred at −3.6 ppm, with a bandwidth of 1.6 ppm.

The frequency spectrum generated from parameters of eqn. 1 aligned with the NSPECT spectrum for the 50% solution (FIGS. 10A-D). By fitting a broad frequency $f_{collagen}$ in the $T_2^*$ model, the cluster of collagen peaks between −2.6 and −4 ppm were treated as one wide peak centred at −3.6 ppm, with a bandwidth of 1.6 ppm. Although there were other collagen peaks near −1 ppm and +3.6 ppm in the NSPECT spectrum, it was not necessarily to characterize all of the peaks; and a chemical shift of −3.6 ppm was an adequate marker of collagen.

Figure 10E:
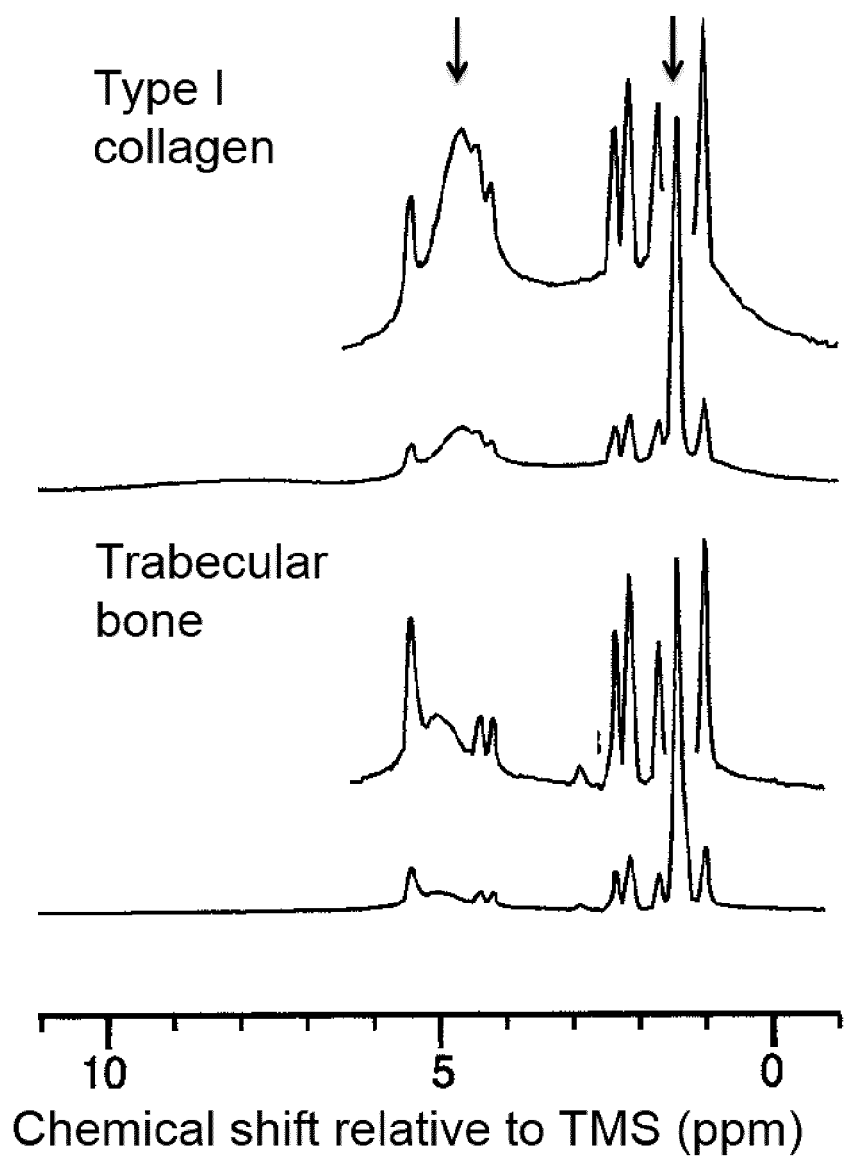
FIG. 10E plots spectra for type I collagen and trabecular bone, adapted from FIG. 9 of Kaflak-Hachulska [17]. The upper spectrum of each sample is magnified four times relative to its lower spectrum. The bound water and tallest collagen peaks are located at 4.7 ppm and 1.5 ppm, respectively.

These spectra were comparable to the spectrum shown in FIG. 10E, which is a proton MR spectrum of collagen type I powder from Kaflak-Hachulska et al., produced under magic-angle spinning at 40 kHz. As the type I powder was analyzed as a solid in that paper, it is believed that the water peak originated from bound water, rather than free water. The collagen peaks were between 2.2 ppm and 1 ppm relative to TMS, corresponding to a range of −2.5 ppm to −3.7 ppm relative to water (where water is chemically shifted 4.7 ppm from TMS).

For the 10% to 50% concentrations, the mean $T_2^*{}_{collagen}$ and $f_{collagen}$ were 0.75±0.05 ms and 1.061±0.004 kHz, respectively. As evident from the low standard deviations, these values were relatively constant. The mean $f_{collagen}$ corresponded to a chemical shift of −3.56±0.01 ppm, which was close to the −3.2 ppm chemical shift of type I collagen found by Kaflak-Hachulska et al. From the NSPECT spectrum, five collagen peaks were observed between −2.6 ppm and −4.0 ppm; these corresponded well with the five peaks between −2.3 ppm and −3.7 ppm in Kaflak-Hachulska et al.'s spectrum (FIG. 10E). It is noted that the collagen solutions were composed of type I and III collagen from bovine hide, whereas Kaflak-Hachulska et al. used type I collagen from bovine Achilles tendon. Differences in chemical shift could be attributed to variations in amino acid composition between the collagen types, sample purity, and origin. Moreover, the type I collagen spectrum was generated under magic-angle spinning at 40 kHz, achieving narrower linewidths than those without spinning.

The mean $T_2^*{}_{collagen}$ of 0.75±0.05 ms was attributed to the protons in collagen, due to the association of $T_2^*{}_{collagen}$ with $f_{collagen}$. As $T_2^*{}_{collagen}$ was consistent over changing collagen concentrations, the value appeared independent of exchange effects. However, the uncertainty in $T_2^*{}_{collagen}$ (~0.07 ms) did not change with increasing collagen concentration, indicating that there was a systematic error affecting the precision of $T_2^*{}_{collagen}$. One would normally expect the uncertainty to decrease, as the random error (due to noise) would decrease with increasing collagen signal. In this case, the systematic error was greater than the random error, and was most likely due to the unmodelled signal in the $T_2^*$ decay.

From FIG. 1A, it is observed that eqn. 1 fitted the $T_2^*$ decay, up to a TE of 3 ms. However, for TEs>3 ms, there was an additional oscillatory component that was not accounted for in the model. Without intending to be limited by theory, this additional oscillatory component may be attributed to protons in collagen-associated water, and/or chemical exchange and cross-relaxation between the collagen and long $T_2^*$ components. Notably, both chemical exchange and cross-relaxation may occur: (1) between the hydration layer water protons and bulk water protons, and (2) between the hydration layer water protons and protein protons [19]. In the bi-exponential $T_2^*$ function of eqn. 1, all of these contributions would be aggregated into the long $T_2^*$ component.

Evidence for exchange was demonstrated by comparing $T_2^*$ decays at varying concentrations of collagen solution. As can be seen from FIG. 7, as the collagen concentration increased, the additional short oscillatory $T_2^*$ component was more apparent and the aggregate $T_2^*{}_{long}$ decreased from 38.2 ms to 11.3 ms. In an ideal bi-exponential $T_2^*$ model, one would expect $T_2^*{}_{long}$ to remain constant; its large range may indicate that the term was accounting for collagen-associated water or exchange that was not modelled. Nonetheless, the "pure" collagen short $T_2^*$ component in this model appeared to be sufficient to characterize collagen content, at least for concentrations 10% m/v, supporting the use of this simplified model with a single frequency offset term and no consideration of collagen-associated water nor exchange.

Example 9: Results from Heart Tissue Analysis

Both histological and UTE MR $T_2^*$ analyses were performed on five canine heart tissue ROIs, in order to determine their collagen content. A histological image pertaining to an exemplary ROI is illustrated in FIG. 11A. FIG. 11B is an enlarged view of the ROI, used for collagen area quantification. Nuclei and particle contamination were removed from the ROI via a threshold on dark pixels in the red channel and manual segmentation respectively, shown in FIG. 11C. This resulting image was used for collagen area quantification via a pixel threshold algorithm in ImageJ, described in above.

The collagen area fraction for the ROI was determined to be 4±2%, where the uncertainty represents the range of collagen area fractions achieved with pixel thresholds delineating collagen only (while excluding the background). The pixel threshold mask representing a 4% collagen area fraction is illustrated in FIG. 10E. Due to the lack of variability in collagen content across ROIs, the collagen area fractions for all five ROIs were within the 4±2% range.

Figure 12A:
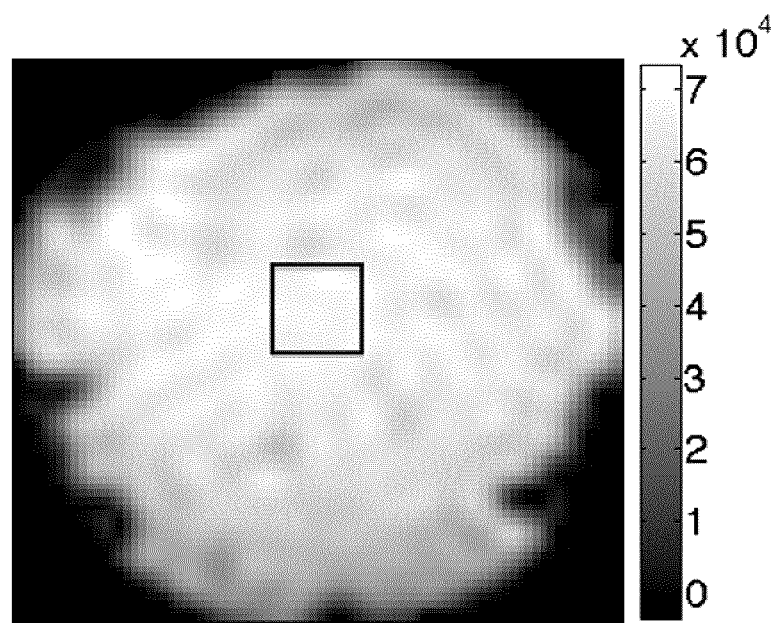
FIGS. 12A-D show results from heart sample analysis.
Figure 12B:
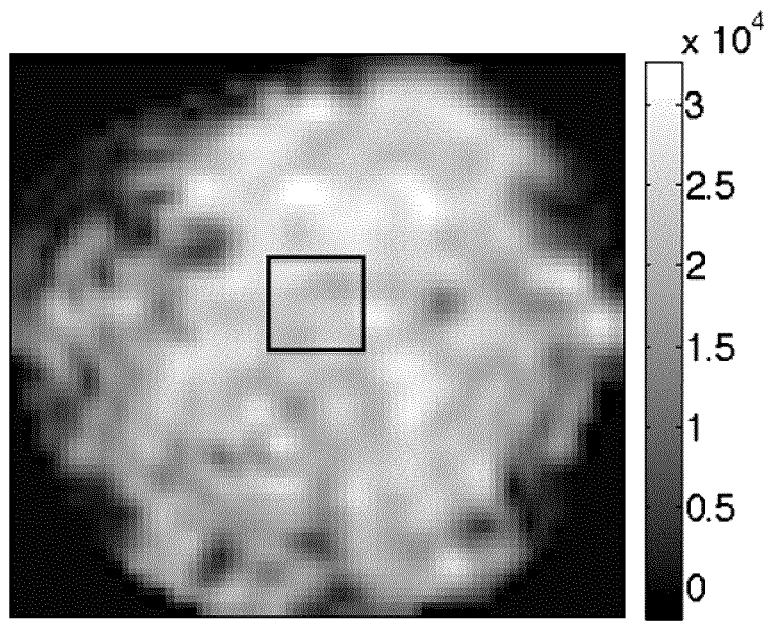
Figure 12C:
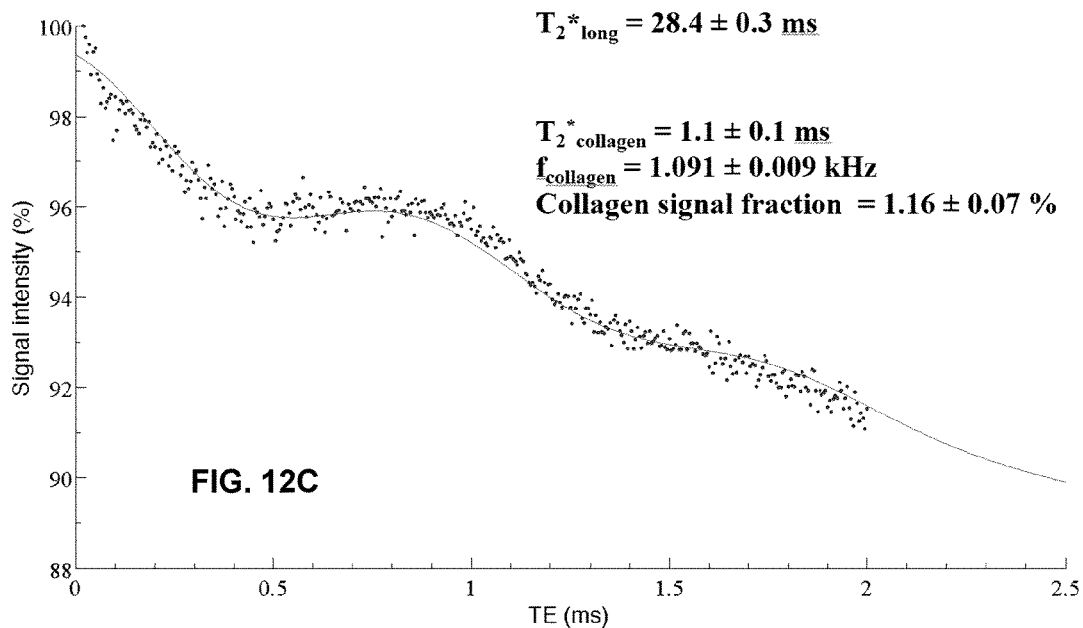

The corresponding axial UTE images of the heart sample from FIGS. 11A-G are shown in FIGS. 12A and 12B, acquired at TEs of 0.02 and 25 ms, respectively. The rectangle indicates the 781.2 µm×781.2 µm ROI. FIG. 12C is the $T_2^*$ fit for the specified ROI, over the short TE range of 0.02 ms to 2 ms. Notable parameters include a collagen $T_2^*$ of 1.1±0.1 ms and a frequency of 1.091±0.009 kHz. The upper bound of $T_2^*{}_{collagen}$ was restricted to 1.1165 ms (equivalent to 1.1±0.1 ms) in the FIG. 12D fit, which included the full TE range of 0.02 ms to 25 ms. The collagen signal fraction was 1.2±0.2%. The long $T_2^*$ was 22.9±0.2 ms.

FIG. 13 outlines the values of the collagen parameters, based on $T_2^*$ analyses of the five heart tissue ROIs for TEs 0.02 ms to 2 ms; fine sampling of this short TE range allowed for accurate characterization of collagen MR properties. Although the mean collagen signal fraction across the ROIs was low (1.0±0.2%), the mean values of $T_2^*{}_{collagen}$ (1.03±0.07 ms) and $f_{collagen}$ (1.12±0.05 kHz) were comparable to those found in collagen solutions.

The preceding results demonstrate that protons in the collagen molecule can be identified via UTE MRI, based on the association of these protons with the short $T_2^*$ signal observed in myocardial fibrosis. As the frequency of the collagen signal is based on the chemical shift of collagen relative to water (e.g. −3.2 ppm [17]), the short $T_2^*$ component can be attributed to collagen directly, rather than a bound water fraction.

Validation of the collagen $T_2^*$ and resonance frequency properties was performed in five ROIs of ex vivo canine heart tissue. Based on the $T_2^*$ decay for TEs 0.02 ms to 2 ms, $T_2^*{}_{collagen}$ and f-collagen were 1.03±0.07 ms and 1.12±0.05 kHz respectively, comparable to the mean values of 0.75±0.05 ms and 1.1061±0.004 kHz in the collagen solutions. FIG. 12C illustrates the $T_2^*$ decay of the short TE range for an exemplary ROI. The low mean collagen signal fraction of 1.0±0.2% was expected, given the limitation of the bi-exponential $T_2^*$ with oscillation model for signal fractions <4%. From histological analysis, each of the five ROIs had a collagen area fraction of 4±2%, which would be deemed healthy. Note that the uncertainty range was large, indicating that many pixel thresholds were reasonable in selecting for the collagen pixels only. Assuming the calibration curve for collagen solutions holds for tissue, the mean collagen signal fraction would correspond to a collagen concentration of 2±1%. While the mass/volume collagen concentration and the collagen area fraction may not be directly comparable, these two values were of the same order of magnitude; hence, UTE analysis yielded a reasonable estimate of collagen content.

Figure 12D:
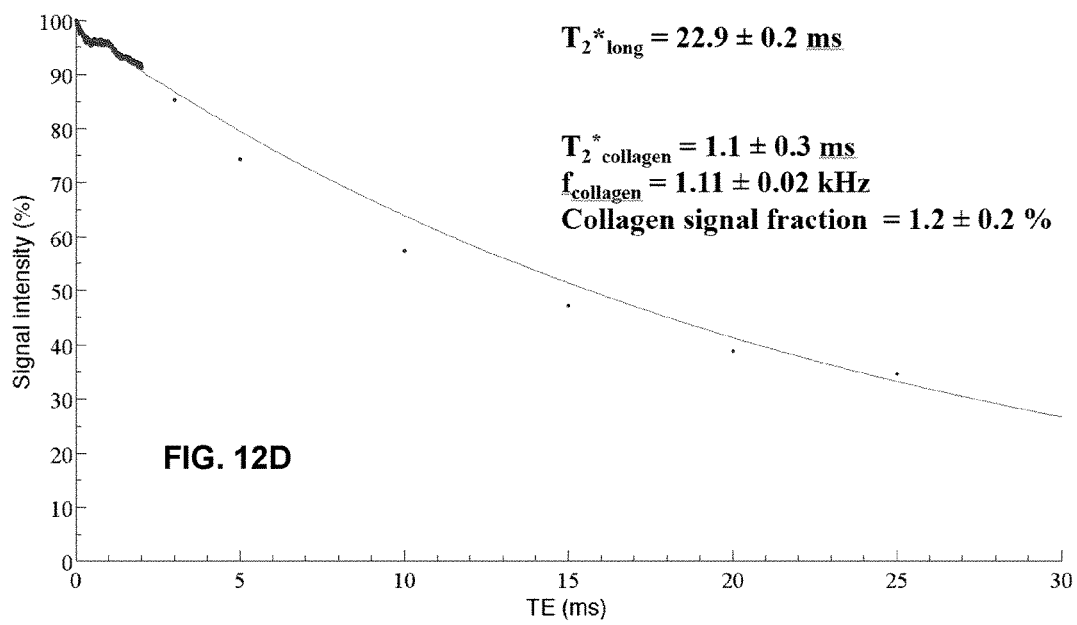

The $T_2^*$ decay of the full TE range from 0.02 ms to 25 ms is shown in FIG. 12D for completeness. As $T_2^*{}_{collagen}$ was determined accurately in the finely sampled short TE range and affected the determination of $S_{0,collagen}$, it seemed reasonable to restrict the value of $T_2^*{}_{collagen}$ for the full TE range. Although $T_2^*{}_{long}$ was not modelled perfectly when the full TE range was fitted, the fit was deemed to be sufficient to characterize the signal component due to collagen, which was already accurately modelled in the short TE range fit. Notably, the $T_2^*$ decay of muscle appeared bi-exponential; the $T_2^*$ decay of muscle is multi-exponential in nature, due to intracellular compartments of muscle-associated water [25]. As muscle-associated-water signal fractions should not contribute to the collagen signal fraction, the $T_2^*$ behaviour of cardiac muscle was simplified to a mono-exponential term.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

[1] N. Mewton, C. Y. Liu, P. Croisille, D. Bluemke, and J. A. C. Lima, "Assessment of Myocardial Fibrosis With Cardiovascular Magnetic Resonance," Journal of the American College of Cardiology, vol. 57, no. 8, pp. 891-903, February 2011.

[2] A. S. Flett, M. P. Hayward, M. T. Ashworth, M. S. Hansen, A. M. Taylor, P. M. Elliott, C. McGregor, and J. C. Moon, "Equilibrium Contrast Cardiovascular Magnetic Resonance for the Measurement of Diffuse Myocardial Fibrosis: Preliminary Validation in Humans," Circulation, vol. 122, no. 2, pp. 138-144, July 2010.

[3] M. A. Rossi, "Connective tissue skeleton in the normal left ventricle and in hypertensive left ventricular hypertrophy and chronic chagasic myocarditis," Medical science monitor: international medical journal of experimental and clinical research, vol. 7, no. 4, p. 820, 2001.

[4] A. M. Segura, O. H. Frazier, and L. M. Buja, "Fibrosis and heart failure," Heart Fail Rev, November 2012.

[5] J. Díez, B. López, A. González, and R. Querejeta, "Clinical aspects of hypertensive myocardial fibrosis," Curr. Opin. Cardiol., vol. 16, no. 6, pp. 328-335, November 2001.

[6] HeartStroke Foundation}, "Statistics on Heart Disease and Stroke in Canada."

[7] D. M. Sado, A. S. Flett, and J. C. Moon, "Novel imaging techniques for diffuse myocardial fibrosis," Future Cardiol, vol. 7, no. 5, pp. 643-650, September 2011.

[8] T. D. Karamitsos and S. Neubauer, "Detecting diffuse myocardial fibrosis with CMR: the future has only just begun," JACC Cardiovasc Imaging, vol. 6, no. 6, pp. 684-686, June 2013.

[9] L. Iles, H. Pfluger, A. Phrommintikul, J. Cherayath, P. Aksit, S. N. Gupta, D. M. Kaye, and A. J. Taylor, "Evaluation of Diffuse Myocardial Fibrosis in Heart Failure With Cardiac Magnetic Resonance Contrast-Enhanced T1 Mapping," Journal of the American College of Cardiology, vol. 52, no. 19, pp. 1574-1580, November 2008.

[10] M. Ugander, A. J. Oki, L. Y. Hsu, P. Kellman, A. Greiser, A. H. Aletras, C. T. Sibley, M. Y. Chen, W. P. Bandettini, and A. E. Arai, "Extracellular volume imaging by magnetic resonance imaging provides insights into overt and sub-clinical myocardial pathology," European Heart Journal, vol. 33, no. 10, pp. 1268-1278, May 2012.

[12] S. de Jong, J. J. Zwanenburg, F. Visser, R. V. der Nagel, H. V. van Rijen, M. A. Vos, J. M. de Bakker, and P. R. Luijten, "Direct detection of myocardial fibrosis by MRI," J. Mol. Cell. Cardiol., vol. 51, no. 6, pp. 974-979, December 2011.

[13] B. J. van Nierop, J. L. Nelissen, N. A. Bax, L. de Graaf, K. Nicolay, and G. J. Strijkers, "In vivo ultra short TE (UTE) MRI of mouse myocardial infarction," Proceedings of the International Society of Magnetic Resonance in Medicine, pp. 1-1, May 2012.

[14] B. J. van Nierop, J. L. Nelissen, N. A. Bax, A. G. Motaal, L. de Graaf, K. Nicolay, and G. J. Strijkers, "In vivo ultra short TE (UTE) MRI detects diffuse fibrosis in hypertrophic mouse hearts," Proceedings of the International Society of Magnetic Resonance in Medicine, pp. 1-1, April 2013.

[15] M. Gajdošík, M. Chmelík, I. Just-Kukurová, W. Bogner, L. Valkovic, S. Trattnig, and M. Krššák, "In vivo relaxation behavior of liver compounds at 7 tesla, measured by single-voxel proton MR spectroscopy," J. Magn. Reson. Imaging, pp. n/a-n/a, November 2013.

[16] Y. Qian, A. A. Williams, C. R. Chu, and F. E. Boada, "Multicomponent T2* mapping of knee cartilage: technical feasibility ex vivo," Magn. Reson. Med., vol. 64, no. 5, pp. 1426-1431, November 2010.

[17] A. Kaflak-Hachulska, A. Samoson, and W. Kolodziejski, "1H MAS and 1H? 31P CP/MAS NMR Study of Human Bone Mineral," Calcified Tissue International, vol. 73, no. 5, pp. 476-486, October 2003.

[18] G. J. Stanisz, E. E. Odrobina, J. Pun, M. Escaravage, S. J. Graham, M. J. Bronskill, and R. M. Henkelman, "T1, T2 relaxation and magnetization transfer in tissue at 3 T," Magn. Reson. Med., vol. 54, no. 3, pp. 507-512, 2005.

[19] J. Zhong, J. C. Gore, and I. M. Armitage, "Relative contributions of chemical exchange and other relaxation mechanisms in protein solutions and tissues," Magn. Reson. Med., vol. 11, no. 3, pp. 295-308, September 1989.

[20] K. T. Weber, J. E. Jalil, J. S. Janicki, and R. Pick, "Myocardial collagen remodeling in pressure overload hypertrophy A case for interstitial heart disease," American journal of hypertension, vol. 2, no. 12, pp. 931-940, 1989.

[21] N. R. Ghugre, M. Pop, J. Barry, K. A. Connelly, and G. A. Wright, "Quantitative magnetic resonance imaging can distinguish remodeling mechanisms after acute myocardial infarction based on the severity of ischemic insult," Magn. Reson. Med., November 2012.

[22] A. Ramadeen, G. Laurent, C. C. dos Santos, X. Hu, K. A. Connelly, B. J. Holub, I. Mangat, and P. Dorian, "n-3 Polyunsaturated fatty acids alter expression of fibrotic and hypertrophic genes in a dog model of atrial cardiomyopathy," Heart Rhythm, vol. 7, no. 4, pp. 520-528, April 2010.

[23] "Technical Details BioSpec MRI—Multi Purpose High Field MRI/MRS Research Systems|Bruker Corporation," bruker.com. [Online]. Available: http://www.bruker.com/products/mr/preclinical-mri/biospec/technical-details.html. [Accessed: 27 Jul. 2014].

[24] "Polysciences, Inc.—FAQ: Picrosirius Red Stain Kit. Technical Data Sheet 837," polysciences.com. [Online]. Available: http://www.polysciences.com/SiteData/docs/837/013378013a29f7e25f8b87d15979dc58/837.pdf. [Accessed: 27 Jul. 2014].

[25] W. C. Cole, A. D. LeBlanc, and S. G. Jhingran, "The origin of biexponential T2 relaxation in muscle water," Magn. Reson. Med., vol. 29, no. 1, pp. 19-24, January 1993.

[26] V. Hoerr, N. Nagelmann, A. Nauerth, M. T. Kuhlmann, J. Stypmann, and C. Faber, "Cardiac-respiratory self-gated cine ultra-short echo time (UTE) cardiovascular magnetic resonance for assessment of functional cardiac parameters at high magnetic fields," J Cardiovasc Magn Reson, vol. 15, no. 1, p. 59, July 2013.

[27] A. G. Motaal, N. Noorman, W. L. de Graaf, V. Hoerr, L. M. J. Florack, K. Nicolay, and G. J. Strijkers, "Functional imaging of murine hearts using accelerated self-gated UTE cine MRI," Int J Cardiovasc Imaging, September 2014.

Therefore what is claimed is:

1. A method of detecting a presence of collagen in tissue using magnetic resonance imaging, the method comprising:
  obtaining a series of images at a plurality of TE values, wherein at least a subset of said images are acquired with ultra-short TE values that are suitable for sampling an initial decay having a time-dependent modulation associated with collagen;
  processing the series of images and fitting a dependence of the signal on TE to a function having fitting parameters comprising:
    a first decay term associated with the presence of collagen, wherein the first decay term is modulated at a modulation frequency associated with the presence of collagen; and a second decay term, the second decay term having a longer decay than the first term; and processing the fitting parameters to provide a measure associated with an amount of collagen.

2. The method of according to claim 1 wherein the fitting parameters include one or more amplitude parameters associated with the amplitude of the first decay term and the second decay term, wherein processing the fitting parameters comprises:

employing the amplitude parameters to determine a collagen signal fraction due to collagen protons.

3. The method of according to claim 2 wherein the measure associated with the amount of collagen is obtained by:

determining the amount of collagen based on a previously determined calibration between the collagen signal fraction to the amount of collagen present in reference samples.

4. The method of according to claim 1 wherein the first decay term is associated with the T2* of collagen protons.

5. The method of according to claim 1 wherein the fitting is performed in a single step by imaging a region of interest expected or known to contain collagen.

6. The method of according to claim 1 wherein the series of TE images are obtained such that the temporal density of data points decreases with TE:

wherein the time interval between successive TE points, for a subset of the images with the lowest TE values, are less than or equal to the interval satisfying the Nyquist criteria based on an estimated or predetermined value of the modulation frequency of collagen; and wherein fitting is performed by:

performing an initial fitting step in which the signals from the subset of images are fitted;

performing a second fitting step in which the signals are fitted over the full range of TE values, wherein the decay constant of the first decay term is fixed according to the decay constant value obtained during the initial fitting step.

7. The method of according to claim 6 wherein the initial fitting step is performed by imaging a region of interest expected or known to contain collagen.

8. The method of according to claim 6 wherein the initial fitting step is performed by imaging a region of interest expected or known to contain fibrosis.

9. The method of according to claim 6 wherein the decay constant of the first decay term is fixed according to the decay constant value obtained during the initial fitting step.

10. The method of according to claim 6 wherein the subset of the TE images have TE values less than approximately 2 ms.

11. The method of according to claim 6 wherein the subset of the TE images have TE values less than approximately 4 ms.

12. The method of according to claim 5 wherein the modulation frequency is fixed according to the modulation frequency value obtained during the initial fitting step.

13. The method of according to claim 1 wherein the series of TE images are obtained such that the temporal density of data points decreases with TE:

wherein the time interval between successive TE points, for a subset of the images with the lowest TE values, are less than or equal to the interval satisfying the Nyquist criteria based on an estimated or predetermined value of the modulation frequency of collagen; and wherein fitting is performed by:

performing an initial fitting step in which the signals from the subset of images are fitted;

performing a second fitting step in which the signals are fitted over the full range of TE values, wherein the modulation frequency is fixed according to the modulation frequency value obtained during the initial fitting step.

14. The method of according to claim 1 wherein the series of TE images are obtained with increasing TE, and wherein the total number of TE points is greater than or equal to 4 and less than or equal to 10.

15. The method of according to claim 1 wherein the modulation frequency is obtained as a fitting parameter.

16. The method according to claim 15 wherein the modulation frequency is constrained to lie within a predetermined frequency range associated with an estimated or measured chemical shift of collagen protons.

17. The method of according to claim 16 wherein the estimated or measured chemical shift of collagen protons is between approximately −2.6 ppm and −4.0 ppm.

18. The method of according to claim 1 wherein the modulation frequency is not a fitting parameter, and is based on an estimated or predetermined value of the modulation frequency of collagen protons.

19. The method of according to claim 18 wherein the modulation frequency is fixed to a value based on a chemical shift of approximately −3.4 ppm.

20. The method of according to claim 1 wherein a decay constant of the first decay term is obtained as a fitting parameter.

21. The method according to claim 20 wherein the decay constant is constrained to lie within an expected or predetermined range of the values of the T2* of collagen protons.

22. The method according to claim 20 wherein the range of values of the T2* of collagen protons is between approximately 0.5 ms and 3.0 ms.

23. The method of according to claim 1 wherein the decay constant is not a fitting parameter, and is based on an estimated or predetermined value of the T2* of collagen protons.

24. The method according to claim 23 wherein the estimated or predetermined value of the T2* of collagen protons lies between 0.5 ms and 3.0 ms.

25. The method of according to claim 2 wherein the collagen signal fraction is obtained by dividing the first amplitude by the sum of the first amplitude and the second amplitude.

26. The method of according to claim 2 wherein the total amplitude is normalized when calculating the collagen signal fraction.

27. The method of according to claim 1 wherein the function is absent of additional decay terms.

28. The method according to claim 1 wherein the function includes one or more additional decay terms, wherein each additional decay term exhibits a decay that is longer than the decay of the first decay term.

29. The method according to claim 28 wherein one or more of the additional decay terms are associated with a known source having a previously determined chemical shift, wherein the known source is other than the collagen protons.

30. The method according to claim 1 wherein the dependence of the signal on TE is determined by averaging over a set of pixels.

31. The method according to claim 1 wherein the dependence of the signal on TE is determined separately for each pixel of a set of pixels.

32. The method according to claim 1 wherein the tissue is cardiac tissue.

33. The method according to claim 32 wherein the second decay term is attributed to cardiac muscle.

34. The method according to claim 32 further comprising determining a measure of myocardial fibrosis based on the measure of the amount of collagen.

35. A method of detecting a presence of collagen in tissue using magnetic resonance imaging, the method comprising:
- performing spectroscopy or spectroscopic imaging and measuring the free induction decay within at least one region of interest;
- fitting a dependence of a signal on time to a function characterized by fitting parameters comprising:
  - a first decay term associated with the presence of collagen, wherein the first decay term is modulated at a modulation frequency; and
  - a second decay term, the second decay term having a longer decay than the first term; and
- processing the fitting parameters to provide a measure associated with an amount of collagen.

\* \* \* \* \*